United States Patent
Denis

(10) Patent No.: US 11,247,289 B2
(45) Date of Patent: Feb. 15, 2022

(54) REMOTE POWER SUPPLY PARAMETER ADJUSTMENT

(71) Applicant: ILLINOIS TOOL WORKS INC., Glenview, IL (US)

(72) Inventor: Marc Lee Denis, Lena, WI (US)

(73) Assignee: Illinois Tool Works Inc., Glenview, IL (US)

( * ) Notice: Subject to any disclaimer, the term of this patent is extended or adjusted under 35 U.S.C. 154(b) by 0 days.

(21) Appl. No.: 14/516,333

(22) Filed: Oct. 16, 2014

(65) Prior Publication Data

US 2016/0107258 A1 Apr. 21, 2016

(51) Int. Cl.
| | |
|---|---|
| *G06F 3/00* | (2006.01) |
| *B23K 9/095* | (2006.01) |
| *B23K 9/10* | (2006.01) |
| *B23K 9/32* | (2006.01) |
| *A61F 9/06* | (2006.01) |

(52) U.S. Cl.
CPC .............. *B23K 9/1087* (2013.01); *A61F 9/06* (2013.01); *A61F 9/067* (2013.01); *B23K 9/0956* (2013.01); *B23K 9/1056* (2013.01); *B23K 9/32* (2013.01); *B23K 9/322* (2013.01)

(58) Field of Classification Search
CPC . B23K 9/10; B23K 9/32; B23K 9/322; B23K 9/09; B23K 9/095; B23K 9/0956; A61F 9/06; A61F 9/067; G06F 3/11; G06F 3/12; G06F 3/16; G06F 3/17
USPC .............. 219/132, 147, 136, 700, 770, 771; 99/483
See application file for complete search history.

(56) References Cited

U.S. PATENT DOCUMENTS

| | | | |
|---|---|---|---|
| 1,340,270 | A | 5/1920 | Emil |
| 2,045,800 | A | 6/1936 | Walther |
| 2,045,801 | A | 6/1936 | Richter |

(Continued)

FOREIGN PATENT DOCUMENTS

| | | |
|---|---|---|
| CA | 2298208 | 8/2000 |
| CA | 2311685 | 12/2001 |

(Continued)

OTHER PUBLICATIONS

"Low Cost Virtual Reality Welding Training System," NSRP Joint Panel Meeting, Apr. 21, 2010, http://www.nsrp.org/6-Presentations/Joint/042110_Low_Cost_Virtual_Reality_Welder_Training_System_Fast.pdf.

(Continued)

*Primary Examiner* — Robert J Utama
*Assistant Examiner* — Ayub A Maye
(74) *Attorney, Agent, or Firm* — McAndrews, Held & Malloy, Ltd.

(57) ABSTRACT

A welding system includes power supply configured to provide a welding power output. The welding system also includes a welding helmet having an electronic display and an inertial measurement unit. The electronic display is configured to display a representation of the power supply and to display one or more indications of one or more parameters of the power supply. The inertial measurement unit is configured to detect movement of the welding helmet. The welding system also includes a processing system communicatively coupled to the inertial measurement unit and configured to adjust at least one parameter of the one or more parameters based at least in part on the movement of welding helmet.

20 Claims, 4 Drawing Sheets

(56) References Cited

U.S. PATENT DOCUMENTS

| | | |
|---|---|---|
| 2,045,802 A | 6/1936 | Walther |
| 2,333,192 A | 10/1942 | Moberg |
| 2,351,910 A | 6/1944 | Blankenbuehler |
| 3,391,691 A | 7/1968 | Young |
| 3,651,290 A | 3/1972 | Durbin |
| 3,679,865 A | 7/1972 | Jesnitzer |
| 3,867,769 A | 2/1975 | Schow |
| 4,028,522 A | 6/1977 | Chihoski |
| 4,041,615 A | 8/1977 | Whitehill |
| 4,044,377 A | 8/1977 | Bowerman |
| 4,124,944 A | 11/1978 | Blair |
| 4,132,014 A | 1/1979 | Schow |
| 4,144,766 A | 3/1979 | Wehrmeister |
| 4,163,886 A | 8/1979 | Omae |
| 4,224,501 A | 9/1980 | Lindbom |
| 4,253,648 A | 3/1981 | Meeks |
| 4,294,440 A | 10/1981 | Severt |
| 4,375,026 A | 2/1983 | Kearney |
| 4,375,165 A | 3/1983 | deSterke |
| 4,389,561 A | 6/1983 | Weman |
| 4,396,945 A | 8/1983 | DiMatteo |
| 4,412,121 A | 10/1983 | Kremers |
| 4,452,589 A | 6/1984 | Denison |
| 4,459,114 A | 7/1984 | Barwick |
| 4,471,207 A | 9/1984 | Hawkes |
| 4,484,059 A | 11/1984 | Lillquist |
| 4,518,361 A | 5/1985 | Conway |
| 4,541,055 A | 9/1985 | Wolfe |
| 4,555,614 A | 11/1985 | Morris |
| 4,577,499 A | 3/1986 | Silke |
| 4,590,356 A | 5/1986 | Povlick |
| 4,591,689 A | 5/1986 | Brown |
| 4,594,497 A | 6/1986 | Takahashi |
| 4,595,186 A | 6/1986 | Reed |
| 4,595,368 A | 6/1986 | Cole |
| 4,595,820 A | 6/1986 | Richardson |
| 4,609,806 A | 9/1986 | Grabkowski |
| 4,628,176 A | 12/1986 | Kojima |
| 4,638,146 A | 1/1987 | Koyama |
| 4,641,292 A * | 2/1987 | Tunnell ................ G10L 15/26 219/132 |
| 4,677,277 A | 6/1987 | Cook |
| 4,680,014 A | 7/1987 | Paton |
| 4,689,021 A | 8/1987 | Vasiliev |
| 4,716,273 A | 12/1987 | Paton |
| 4,721,947 A | 1/1988 | Brown |
| 4,728,768 A | 3/1988 | Cueman |
| 4,739,404 A | 4/1988 | Richardson |
| 4,767,109 A | 8/1988 | Raketich |
| 4,829,365 A | 5/1989 | Eichenlaub |
| 4,830,261 A | 5/1989 | Mello |
| 4,867,685 A | 9/1989 | Brush |
| 4,868,649 A | 9/1989 | Gaudin |
| 4,877,940 A | 10/1989 | Bangs |
| 4,881,678 A | 11/1989 | Gaudin |
| 4,920,249 A | 4/1990 | McLaughlin |
| 4,931,018 A | 6/1990 | Herbst |
| 4,937,427 A | 6/1990 | McVicker |
| 4,943,702 A | 7/1990 | Richardson |
| 4,954,690 A | 9/1990 | Kensrue |
| 4,992,881 A | 2/1991 | Tomasek |
| 4,996,409 A | 2/1991 | Paton |
| 5,061,841 A | 10/1991 | Richardson |
| 5,103,376 A | 4/1992 | Blonder |
| 5,185,561 A | 2/1993 | Good |
| 5,208,436 A | 5/1993 | Blankenship |
| 5,211,564 A | 8/1993 | Martinez |
| 5,231,928 A | 8/1993 | Phillips |
| 5,283,418 A | 2/1994 | Bellows |
| 5,302,799 A | 4/1994 | Kennedy |
| 5,304,774 A | 4/1994 | Durheim |
| 5,306,893 A | 4/1994 | Morris |
| 5,320,538 A | 6/1994 | Baum |
| 5,343,011 A | 8/1994 | Fujii |
| 5,380,978 A | 1/1995 | Pryor |
| 5,397,872 A | 3/1995 | Baker |
| 5,404,181 A | 4/1995 | Hung |
| 5,426,732 A | 6/1995 | Boies |
| 5,448,405 A | 9/1995 | Clausen |
| 5,464,957 A | 11/1995 | Kidwell |
| 5,508,757 A | 4/1996 | Chen |
| 5,514,846 A | 5/1996 | Cecil |
| 5,517,420 A | 5/1996 | Kinsman |
| 5,521,843 A | 5/1996 | Hashima |
| 5,533,146 A | 7/1996 | Iwai |
| 5,543,863 A | 8/1996 | Lin |
| 5,546,476 A | 8/1996 | Mitaka |
| 5,571,431 A | 11/1996 | Lantieri |
| 5,592,241 A | 1/1997 | Kita |
| 5,617,335 A | 4/1997 | Hashima |
| 5,659,479 A | 8/1997 | Duley |
| 5,668,612 A | 9/1997 | Hung |
| 5,674,415 A | 10/1997 | Leong |
| 5,675,229 A | 10/1997 | Thorne |
| 5,681,490 A | 10/1997 | Chang |
| 5,708,253 A | 1/1998 | Bloch |
| 5,709,219 A | 1/1998 | Chen |
| 5,747,042 A | 5/1998 | Choquet |
| 5,823,785 A | 10/1998 | Matherne, Jr. |
| 5,832,139 A | 11/1998 | Batterman |
| 5,856,844 A | 1/1999 | Batterman |
| 5,930,093 A | 7/1999 | Morrissett |
| 5,961,859 A | 10/1999 | Chou |
| 5,973,677 A | 10/1999 | Gibbons |
| 5,999,909 A | 12/1999 | Rakshit |
| 6,003,052 A | 12/1999 | Yamagata |
| 6,018,729 A | 1/2000 | Zacharia |
| 6,019,359 A | 2/2000 | Fly |
| 6,024,273 A | 2/2000 | Ludewig |
| 6,039,494 A | 3/2000 | Pearce |
| 6,046,754 A | 4/2000 | Stanek |
| 6,049,059 A | 4/2000 | Kim |
| 6,051,805 A | 4/2000 | Vaidya |
| 6,101,455 A | 8/2000 | Davis |
| 6,107,601 A | 8/2000 | Shimogama |
| 6,130,407 A | 10/2000 | Villafuerte |
| 6,136,946 A | 10/2000 | Yao |
| 6,153,848 A | 11/2000 | Nagae |
| 6,155,475 A | 12/2000 | Ekelof |
| 6,163,946 A | 12/2000 | Pryor |
| 6,226,395 B1 | 5/2001 | Gilliland |
| 6,236,017 B1 | 5/2001 | Smartt |
| 6,242,711 B1 | 6/2001 | Cooper |
| 6,271,500 B1 | 8/2001 | Hirayama |
| 6,288,359 B1 | 9/2001 | Koch |
| 6,290,740 B1 | 9/2001 | Schaefer |
| 6,301,763 B1 | 10/2001 | Pryor |
| 6,315,186 B1 | 11/2001 | Friedl |
| 6,329,635 B1 | 12/2001 | Leong |
| 6,337,458 B1 | 1/2002 | Lepeltier |
| 6,371,765 B1 | 4/2002 | Wall |
| 6,417,894 B1 | 7/2002 | Goff |
| 6,423,936 B1 | 7/2002 | Reed |
| 6,441,342 B1 | 8/2002 | Hsu |
| 6,445,964 B1 | 9/2002 | White |
| 6,469,752 B1 | 10/2002 | Ishikawa |
| 6,476,354 B1 | 11/2002 | Jank |
| 6,479,793 B1 | 11/2002 | Wittmann |
| 6,506,997 B2 | 1/2003 | Matsuyama |
| 6,516,300 B1 | 2/2003 | Rakshit |
| 6,572,379 B1 | 6/2003 | Sears |
| 6,583,386 B1 | 6/2003 | Ivkovich |
| 6,596,972 B1 | 7/2003 | Di Novo |
| 6,614,002 B2 | 9/2003 | Weber |
| 6,621,049 B2 | 9/2003 | Suzuki |
| 6,622,906 B1 | 9/2003 | Kushibe |
| 6,647,288 B2 | 11/2003 | Madill |
| 6,670,574 B1 | 12/2003 | Bates |
| 6,697,761 B2 | 2/2004 | Akatsuka |
| 6,703,585 B2 | 3/2004 | Suzuki |
| 6,710,298 B2 * | 3/2004 | Eriksson ............. A61F 9/06 219/130.01 |
| 6,720,878 B2 * | 4/2004 | Jumpertz ............ A42B 3/0433 340/286.05 |

(56) References Cited

U.S. PATENT DOCUMENTS

| | | | |
|---|---|---|---|
| 6,728,582 B1 | 4/2004 | Wallack | |
| 6,734,393 B1 * | 5/2004 | Friedl | A61F 9/067 219/130.01 |
| 6,744,011 B1 | 6/2004 | Hu | |
| 6,748,249 B1 | 6/2004 | Eromaki | |
| 6,750,428 B2 | 6/2004 | Okamoto | |
| 6,753,909 B1 | 6/2004 | Westerman | |
| 6,768,974 B1 | 7/2004 | Nanjundan | |
| 6,839,049 B1 | 1/2005 | Koizumi | |
| 6,857,553 B1 | 2/2005 | Hartman | |
| 6,868,726 B2 | 3/2005 | Lemkin | |
| 6,910,971 B2 | 6/2005 | Alsenz | |
| 6,927,360 B2 | 8/2005 | Artelsmair | |
| 6,937,329 B2 | 8/2005 | Esmiller | |
| 6,967,635 B2 | 11/2005 | Hung | |
| 6,977,357 B2 | 12/2005 | Hsu | |
| 6,995,536 B2 | 2/2006 | Challoner | |
| 7,015,419 B2 | 3/2006 | Hackl | |
| 7,025,053 B1 | 4/2006 | Altamirano | |
| 7,032,814 B2 | 4/2006 | Blankenship | |
| 7,045,742 B2 | 5/2006 | Feichtinger | |
| 7,081,888 B2 | 7/2006 | Cok | |
| 7,120,473 B1 | 10/2006 | Hawkins | |
| 7,132,617 B2 | 11/2006 | Lee | |
| 7,132,623 B2 | 11/2006 | DeMiranda | |
| 7,150,047 B2 | 12/2006 | Fergason | |
| 7,173,215 B1 | 2/2007 | Kapoor | |
| 7,181,413 B2 | 2/2007 | Hadden | |
| 7,226,176 B1 | 6/2007 | Huang | |
| 7,261,261 B2 | 8/2007 | Ligertwood | |
| 7,342,210 B2 | 3/2008 | Fergason | |
| 7,358,458 B2 | 4/2008 | Daniel | |
| 7,465,230 B2 | 12/2008 | LeMay | |
| 7,474,760 B2 | 1/2009 | Hertzman | |
| 7,523,069 B1 | 4/2009 | Friedl | |
| 7,564,005 B2 | 7/2009 | Cabanaw | |
| 7,574,172 B2 | 8/2009 | Clark | |
| 7,577,285 B2 | 8/2009 | Schwarz | |
| 7,637,622 B2 * | 12/2009 | Garbergs | A61F 9/061 359/601 |
| D614,217 S | 4/2010 | Peters | |
| 7,698,094 B2 | 4/2010 | Aratani | |
| D615,573 S | 5/2010 | Peters | |
| 7,766,213 B2 | 8/2010 | Henrikson | |
| 7,789,811 B2 | 9/2010 | Cooper | |
| 7,826,984 B2 | 11/2010 | Sjostrand | |
| 7,831,098 B2 | 11/2010 | Melikian | |
| 7,839,416 B2 | 11/2010 | Ebensberger | |
| 7,845,560 B2 | 12/2010 | Emanuel | |
| D631,074 S | 1/2011 | Peters | |
| 7,899,618 B2 | 3/2011 | Ledet | |
| 7,962,967 B2 | 6/2011 | Becker | |
| 8,019,144 B2 | 9/2011 | Sugihara | |
| 8,044,942 B1 | 10/2011 | Leonhard | |
| 8,046,178 B2 | 10/2011 | Dai | |
| 8,100,694 B2 | 1/2012 | Portoghese | |
| 8,110,774 B2 | 2/2012 | Huonker | |
| 8,235,588 B2 | 8/2012 | Louban | |
| 8,248,324 B2 | 8/2012 | Nangle | |
| 8,274,013 B2 | 9/2012 | Wallace | |
| 8,316,462 B2 | 11/2012 | Becker | |
| 8,393,519 B2 | 3/2013 | Allehaux | |
| 8,406,682 B2 | 3/2013 | Elesseily | |
| 8,431,862 B2 | 4/2013 | Kachline | |
| 8,432,476 B2 | 4/2013 | Ashforth | |
| 8,502,866 B2 * | 8/2013 | Becker | A61F 9/06 345/8 |
| 8,512,043 B2 | 8/2013 | Choquet | |
| 8,541,746 B2 | 9/2013 | Andres | |
| 8,569,655 B2 * | 10/2013 | Cole | A61F 9/06 2/8.2 |
| 8,657,605 B2 | 2/2014 | Wallace | |
| 8,680,434 B2 | 3/2014 | Stoger | |
| 8,681,178 B1 | 3/2014 | Tseng | |
| 8,692,157 B2 | 4/2014 | Daniel | |
| 8,698,843 B2 | 4/2014 | Tseng | |
| 8,747,116 B2 | 6/2014 | Zboray | |
| 8,834,168 B2 | 9/2014 | Peters | |
| 8,851,896 B2 | 10/2014 | Wallace | |
| 8,860,760 B2 | 10/2014 | Chen | |
| 8,911,237 B2 | 12/2014 | Postlethwaite | |
| 8,915,740 B2 | 12/2014 | Zboray | |
| 8,946,595 B2 | 2/2015 | Ishida | |
| 8,953,033 B2 | 2/2015 | Yamane | |
| 8,953,909 B2 | 2/2015 | Guckenberger | |
| RE45,398 E | 3/2015 | Wallace | |
| 8,987,628 B2 | 3/2015 | Daniel | |
| 8,990,842 B2 | 3/2015 | Rowley | |
| 8,992,226 B1 | 3/2015 | Leach | |
| 9,011,154 B2 | 4/2015 | Kindig | |
| 9,012,802 B2 | 4/2015 | Daniel | |
| 9,050,678 B2 | 6/2015 | Daniel | |
| 9,050,679 B2 | 6/2015 | Daniel | |
| 9,089,921 B2 | 7/2015 | Daniel | |
| 9,196,169 B2 | 11/2015 | Wallace | |
| 9,218,745 B2 | 12/2015 | Choquet | |
| 9,221,117 B2 | 12/2015 | Conrardy | |
| 9,269,279 B2 | 2/2016 | Rod | |
| 9,293,056 B2 | 3/2016 | Zboray | |
| 9,293,057 B2 | 3/2016 | Zboray | |
| 9,318,026 B2 | 4/2016 | Peters | |
| 9,330,575 B2 | 5/2016 | Peters | |
| 9,336,686 B2 | 5/2016 | Peters | |
| 9,402,122 B2 | 7/2016 | Richardson | |
| 9,511,443 B2 * | 12/2016 | Pfeifer | B23K 9/095 |
| 2001/0026445 A1 | 10/2001 | Naghi | |
| 2001/0032508 A1 | 10/2001 | Lemkin | |
| 2002/0043607 A1 | 4/2002 | Tajima | |
| 2002/0071550 A1 | 6/2002 | Pletikosa | |
| 2002/0105797 A1 | 8/2002 | Navid | |
| 2002/0114653 A1 | 8/2002 | Gatta | |
| 2002/0148745 A1 | 10/2002 | Chang | |
| 2002/0153354 A1 | 10/2002 | Norby | |
| 2003/0011673 A1 | 1/2003 | Eriksson | |
| 2003/0092496 A1 | 5/2003 | Alsenz | |
| 2003/0172032 A1 | 9/2003 | Choquet | |
| 2004/0058703 A1 | 3/2004 | Eromaki | |
| 2004/0068335 A1 | 4/2004 | Ferla | |
| 2004/0069754 A1 | 4/2004 | Bates | |
| 2004/0175684 A1 | 9/2004 | Kaasa | |
| 2004/0223148 A1 | 11/2004 | Takemura | |
| 2004/0227730 A1 | 11/2004 | Sugihara | |
| 2004/0251910 A1 | 12/2004 | Smith | |
| 2005/0006363 A1 | 1/2005 | Hsu | |
| 2005/0012598 A1 | 1/2005 | Berquist | |
| 2005/0016979 A1 | 1/2005 | Stein | |
| 2005/0017152 A1 | 1/2005 | Fergason | |
| 2005/0073506 A1 | 4/2005 | Durso | |
| 2005/0127052 A1 | 6/2005 | Spencer | |
| 2005/0133488 A1 | 6/2005 | Blankenship | |
| 2005/0135682 A1 | 6/2005 | Abrams | |
| 2005/0179654 A1 | 8/2005 | Hawkins | |
| 2005/0197115 A1 | 9/2005 | Clark | |
| 2005/0207102 A1 | 9/2005 | Russo | |
| 2005/0227635 A1 | 10/2005 | Hawkins | |
| 2005/0256611 A1 | 11/2005 | Pretlove | |
| 2006/0010551 A1 | 1/2006 | Bishop | |
| 2006/0081740 A1 | 4/2006 | Bellavance | |
| 2006/0136183 A1 | 6/2006 | Choquet | |
| 2006/0151446 A1 | 7/2006 | Schneider | |
| 2006/0163228 A1 | 7/2006 | Daniel | |
| 2006/0173619 A1 | 8/2006 | Brant | |
| 2006/0212169 A1 | 9/2006 | Luthardt | |
| 2006/0241432 A1 | 10/2006 | Herline | |
| 2007/0038400 A1 | 2/2007 | Lee | |
| 2007/0051711 A1 | 3/2007 | Kachline | |
| 2007/0114215 A1 | 5/2007 | Bill | |
| 2007/0115202 A1 | 5/2007 | Kiesenhofer | |
| 2007/0164006 A1 | 7/2007 | Burgstaller | |
| 2007/0187378 A1 | 8/2007 | Karakas | |
| 2007/0188606 A1 | 8/2007 | Atkinson | |
| 2007/0221636 A1 | 9/2007 | Monzyk | |
| 2007/0247793 A1 | 10/2007 | Carnevali | |
| 2007/0248261 A1 | 10/2007 | Zhou | |

(56) References Cited

U.S. PATENT DOCUMENTS

| | | |
|---|---|---|
| 2007/0264620 A1 | 11/2007 | Maddix |
| 2007/0278196 A1 | 12/2007 | James |
| 2007/0291166 A1 | 12/2007 | Misawa |
| 2008/0030631 A1 | 2/2008 | Gallagher |
| 2008/0038702 A1 | 2/2008 | Choquet |
| 2008/0061113 A9 | 3/2008 | Seki |
| 2008/0077422 A1 | 3/2008 | Dooley |
| 2008/0124698 A1 | 5/2008 | Ebensberger |
| 2008/0128395 A1 | 6/2008 | Aigner |
| 2008/0149602 A1 | 6/2008 | Lenzner |
| 2008/0149608 A1 | 6/2008 | Albrecht |
| 2008/0158502 A1 | 7/2008 | Becker |
| 2008/0168290 A1 | 7/2008 | Jobs |
| 2008/0169277 A1 | 7/2008 | Achtner |
| 2008/0234960 A1 | 9/2008 | Byington |
| 2008/0314887 A1 | 12/2008 | Stoger |
| 2009/0005728 A1 | 1/2009 | Weinert |
| 2009/0057286 A1 | 3/2009 | Ihara |
| 2009/0109128 A1 | 4/2009 | Nangle |
| 2009/0146359 A1 | 6/2009 | Canfield |
| 2009/0152251 A1 | 6/2009 | Dantinne |
| 2009/0161212 A1 | 6/2009 | Gough |
| 2009/0173726 A1 | 7/2009 | Davidson |
| 2009/0189974 A1 | 7/2009 | Deering |
| 2009/0200281 A1 | 8/2009 | Hampton |
| 2009/0200282 A1 | 8/2009 | Hampton |
| 2009/0230107 A1 | 9/2009 | Ertmer |
| 2009/0231423 A1 | 9/2009 | Becker |
| 2009/0249606 A1 | 10/2009 | Diez |
| 2009/0283021 A1 | 11/2009 | Wong |
| 2009/0298024 A1* | 12/2009 | Batzler .................. B23K 9/32 434/234 |
| 2009/0323121 A1 | 12/2009 | Valkenburg |
| 2010/0020483 A1 | 1/2010 | Ma |
| 2010/0048273 A1 | 2/2010 | Wallace |
| 2010/0053541 A1 | 3/2010 | Sundell |
| 2010/0062405 A1 | 3/2010 | Zboray |
| 2010/0062406 A1 | 3/2010 | Zboray |
| 2010/0088793 A1 | 4/2010 | Ghisleni |
| 2010/0123664 A1 | 5/2010 | Shin |
| 2010/0133247 A1 | 6/2010 | Mazumder |
| 2010/0145520 A1 | 6/2010 | Gerio |
| 2010/0201803 A1 | 8/2010 | Melikian |
| 2010/0207620 A1 | 8/2010 | Gies |
| 2010/0224610 A1 | 9/2010 | Wallace |
| 2010/0238119 A1 | 9/2010 | Dubrovsky |
| 2010/0245273 A1 | 9/2010 | Hwang |
| 2010/0283588 A1 | 11/2010 | Gomez |
| 2010/0291313 A1 | 11/2010 | Ling |
| 2010/0314362 A1 | 12/2010 | Albrecht |
| 2011/0000892 A1 | 1/2011 | Mueller |
| 2011/0006047 A1 | 1/2011 | Penrod |
| 2011/0091846 A1 | 4/2011 | Kreindl |
| 2011/0092828 A1 | 4/2011 | Spohn |
| 2011/0114615 A1 | 5/2011 | Daniel |
| 2011/0117527 A1 | 5/2011 | Conrardy |
| 2011/0176720 A1 | 7/2011 | VanOsten |
| 2011/0183304 A1* | 7/2011 | Wallace .................. G09B 19/24 434/234 |
| 2011/0220616 A1 | 9/2011 | Mehn |
| 2011/0220619 A1 | 9/2011 | Mehn |
| 2011/0240605 A1 | 10/2011 | Takayama |
| 2011/0249090 A1 | 10/2011 | Moore |
| 2011/0284508 A1 | 11/2011 | Miura |
| 2011/0286005 A1 | 11/2011 | Yamamoto |
| 2011/0290765 A1 | 12/2011 | Albrecht |
| 2011/0313731 A1 | 12/2011 | Vock |
| 2011/0316516 A1* | 12/2011 | Schiefermuller ......... A61F 9/06 323/318 |
| 2012/0007748 A1 | 1/2012 | Forgues |
| 2012/0012561 A1* | 1/2012 | Wiryadinata ........ B23K 9/1087 219/108 |
| 2012/0048838 A1 | 3/2012 | Ishida |
| 2012/0057240 A1 | 3/2012 | Sundell |
| 2012/0067859 A1 | 3/2012 | Albrecht |
| 2012/0072021 A1 | 3/2012 | Walser |
| 2012/0077174 A1 | 3/2012 | DePaul |
| 2012/0105476 A1 | 5/2012 | Tseng |
| 2012/0113512 A1 | 5/2012 | Tsanev |
| 2012/0122062 A1 | 5/2012 | Yang |
| 2012/0175834 A1 | 7/2012 | Hamm |
| 2012/0180180 A1 | 7/2012 | Steve |
| 2012/0188365 A1 | 7/2012 | Stork |
| 2012/0189993 A1 | 7/2012 | Kindig |
| 2012/0205359 A1 | 8/2012 | Daniel |
| 2012/0231894 A1 | 9/2012 | Nicora |
| 2012/0248080 A1 | 10/2012 | Hutchison |
| 2012/0248083 A1 | 10/2012 | Garvey |
| 2012/0273473 A1 | 11/2012 | Zhang |
| 2012/0280576 A1 | 11/2012 | Wood |
| 2012/0291172 A1 | 11/2012 | Wills |
| 2012/0298640 A1 | 11/2012 | Conrardy |
| 2012/0323496 A1 | 12/2012 | Burroughs |
| 2013/0040270 A1 | 2/2013 | Albrecht |
| 2013/0081293 A1 | 4/2013 | Delin |
| 2013/0182070 A1 | 7/2013 | Peters |
| 2013/0189656 A1 | 7/2013 | Zboray |
| 2013/0189657 A1 | 7/2013 | Wallace |
| 2013/0189658 A1 | 7/2013 | Peters |
| 2013/0200882 A1 | 8/2013 | Almalki |
| 2013/0206741 A1* | 8/2013 | Pfeifer .................. B23K 9/095 219/130.01 |
| 2013/0208569 A1 | 8/2013 | Pfeifer |
| 2013/0209976 A1 | 8/2013 | Postlethwaite |
| 2013/0262000 A1 | 10/2013 | Hutchison |
| 2013/0264315 A1 | 10/2013 | Hung |
| 2013/0264322 A1 | 10/2013 | Bornemann |
| 2013/0288211 A1 | 10/2013 | Patterson |
| 2013/0291271 A1* | 11/2013 | Becker .................. G06F 3/005 2/8.2 |
| 2013/0326842 A1 | 12/2013 | Pearson |
| 2014/0008088 A1 | 1/2014 | Chellew |
| 2014/0017642 A1 | 1/2014 | Postlethwaite |
| 2014/0017645 A1 | 1/2014 | Simpson |
| 2014/0042135 A1 | 2/2014 | Daniel |
| 2014/0069899 A1 | 3/2014 | Mehn |
| 2014/0131337 A1 | 5/2014 | Williams |
| 2014/0134579 A1 | 5/2014 | Becker |
| 2014/0134580 A1 | 5/2014 | Becker |
| 2014/0140719 A1 | 5/2014 | Suzuki |
| 2014/0144896 A1 | 5/2014 | Einav |
| 2014/0184496 A1* | 7/2014 | Gribetz ................ G02B 27/017 345/156 |
| 2014/0220522 A1 | 8/2014 | Peters |
| 2014/0234813 A1 | 8/2014 | Peters |
| 2014/0263224 A1 | 9/2014 | Becker |
| 2014/0263227 A1 | 9/2014 | Daniel |
| 2014/0267773 A1 | 9/2014 | Jeung |
| 2014/0272835 A1 | 9/2014 | Becker |
| 2014/0272836 A1 | 9/2014 | Becker |
| 2014/0272837 A1 | 9/2014 | Becker |
| 2014/0272838 A1 | 9/2014 | Becker |
| 2014/0315167 A1 | 10/2014 | Kreindl |
| 2014/0322684 A1 | 10/2014 | Wallace |
| 2014/0346158 A1* | 11/2014 | Matthews ............ B23K 9/0953 219/130.01 |
| 2014/0346793 A1 | 11/2014 | DeStories |
| 2014/0374396 A1 | 12/2014 | Luo |
| 2015/0056584 A1* | 2/2015 | Boulware ............... B23K 9/173 434/234 |
| 2015/0056585 A1 | 2/2015 | Boulware |
| 2015/0072323 A1 | 3/2015 | Postlethwaite |
| 2015/0154884 A1 | 6/2015 | Salsich |
| 2015/0170539 A1 | 6/2015 | Barrera |
| 2015/0190875 A1 | 7/2015 | Becker |
| 2015/0190876 A1 | 7/2015 | Becker |
| 2015/0190887 A1 | 7/2015 | Becker |
| 2015/0190888 A1 | 7/2015 | Becker |
| 2015/0194072 A1 | 7/2015 | Becker |
| 2015/0194073 A1 | 7/2015 | Becker |
| 2015/0209887 A1 | 7/2015 | DeLisio |
| 2015/0235565 A1 | 8/2015 | Postlethwaite |
| 2015/0248845 A1 | 9/2015 | Postlethwaite |
| 2015/0325153 A1 | 11/2015 | Albrecht |

(56) References Cited

U.S. PATENT DOCUMENTS

| | | |
|---|---|---|
| 2015/0375323 A1 | 12/2015 | Becker |
| 2015/0375324 A1 | 12/2015 | Becker |
| 2015/0375327 A1 | 12/2015 | Becker |
| 2015/0379894 A1 | 12/2015 | Becker |
| 2016/0039034 A1 | 2/2016 | Becker |
| 2016/0039053 A1 | 2/2016 | Becker |
| 2016/0049085 A1 | 2/2016 | Beeson |
| 2016/0093233 A1 | 3/2016 | Boulware |
| 2016/0203734 A1 | 7/2016 | Boulware |
| 2016/0203735 A1 | 7/2016 | Boulware |
| 2016/0236303 A1 | 8/2016 | Matthews |
| 2017/0326674 A1* | 11/2017 | Dunbar ............... A61F 9/06 |

FOREIGN PATENT DOCUMENTS

| | | |
|---|---|---|
| CA | 2517874 | 12/2001 |
| CA | 2549553 | 7/2004 |
| CA | 2554498 | 4/2006 |
| CN | 101203197 | 6/2008 |
| CN | 101323046 | 12/2008 |
| CN | 102378666 | 3/2012 |
| CN | 102958636 A | 3/2013 |
| CN | 102971106 A | 3/2013 |
| CN | 202877704 | 4/2013 |
| CN | 104014906 | 9/2014 |
| DE | 202010011064 | 10/2010 |
| DE | 102010038902 | 2/2012 |
| EP | 0323277 A2 | 7/1989 |
| EP | 0878263 | 11/1998 |
| EP | 0963744 A1 | 12/1999 |
| EP | 1025946 | 8/2000 |
| EP | 1029306 | 8/2000 |
| EP | 1295195 | 6/2001 |
| EP | 1573699 | 9/2005 |
| EP | 1797545 | 6/2007 |
| EP | 1864744 | 12/2007 |
| EP | 2022592 | 2/2009 |
| EP | 2415560 | 2/2014 |
| ES | 2438440 | 1/2014 |
| FR | 1456780 | 7/1966 |
| FR | 2827066 | 1/2003 |
| GB | 2454232 A | 5/2009 |
| JP | S5527422 | 2/1980 |
| JP | H05141909 | 6/1993 |
| JP | H11146387 | 5/1999 |
| JP | 2000298427 | 10/2000 |
| JP | 2004181493 | 7/2004 |
| JP | 2007021542 | 2/2007 |
| JP | 2009125790 | 6/2009 |
| KR | 100876425 B1 | 12/2008 |
| KR | 20110017484 | 2/2011 |
| KR | 20130048580 | 5/2013 |
| SU | 972552 | 11/1982 |
| SU | 1354234 A1 | 11/1987 |
| SU | 1489933 A1 | 6/1989 |
| SU | 1638145 | 3/1991 |
| WO | 9934950 | 7/1999 |
| WO | 9958286 | 11/1999 |
| WO | 03019349 | 1/2003 |
| WO | 2004057554 | 7/2004 |
| WO | 2005102230 A1 | 11/2005 |
| WO | 2005110658 A2 | 11/2005 |
| WO | 2006004427 | 1/2006 |
| WO | 2006034571 | 4/2006 |
| WO | 2007009131 | 1/2007 |
| WO | 2007044135 | 4/2007 |
| WO | 2009022443 | 2/2009 |
| WO | 2009053829 | 4/2009 |
| WO | 2009060231 | 5/2009 |
| WO | 2009092944 | 7/2009 |
| WO | 2009146359 | 12/2009 |
| WO | 2010000003 | 1/2010 |
| WO | 2010020867 | 2/2010 |
| WO | 2010020870 | 2/2010 |
| WO | 2010111722 | 10/2010 |
| WO | 2011112493 | 9/2011 |
| WO | 2011150165 | 12/2011 |
| WO | 2012137060 | 10/2012 |
| WO | 2013138831 | 1/2013 |
| WO | 2013023012 | 2/2013 |
| WO | 2014007830 | 1/2014 |
| WO | 2014074296 | 5/2014 |
| WO | 2014140719 | 9/2014 |

OTHER PUBLICATIONS

"NJC Technology Displayed at ShipTech 2005", Welding Journal, vol. 84, No. 3, Mar. 2005, p. 54, https://app.aws.org/w/r/www/wj/2005/03/WJ_2005_03.pdf.

"Sheet Metal Conference XXII," Conference Program, American Welding Society, May 2006, Detroit.

"Virtual Reality Program to Train Welders for Shipbuilding", American Welding Society, Navy Joining Center, https://app.aws.org/wj/2004/04/052/.

"Virtual Reality Welder Training Initiatives: Virtual Welding Lab Pilot," Paul D. Camp Community College, Advanced Science & Automation Corporation, Northrop Grumman Newport News, Nov. 22, 2006, http://www.nsrp.org/6-Presentations/WD/103106_Virtual_Reality_Welder.pdf.

"Virtual Welding: A Low Cost Virtual Reality Welder Training System," NSRP ASE, Feb. 19, 2009, http://www.nsrp.org/6-Presentations/WD/020409_Virtual_Welding_Wilbur.pdf.

"Virtual Welding—A Low Cost Virtual Reality Welder Training System", Interim Status Report # 4, Technology Investment Agreement 2008-600, Feb. 18, 2009, http://www.nsrp.org/3-Key_Deliverables/FY08_Low-Cost_Virtual_Reality_Welder_Trainer/FY08_Low-Cost_Virtual_Reality_Welder_Trainer-Interim2.pdf.

"Vision for Welding Industry," American Welding Society, Apr. 22, 1999, http://www.aws.org/library/doclib/vision.pdf.

"Welding in Defense Industry," American Welding Society conference schedule, 2004. https://app.aws.org/conferences/defense/live_index.html.

"Welding Technology Roadmap," prepared by Energetics, Inc., Columbia, MD, in cooperation with The American Welding Society and the Edison Welding Institute, Sep. 2000.

123arc.com—"Weld into the future"; 2000.

Advance Program of American Welding Society Programs and Events, Nov. 11-14, 2007, Chicago.

Aiteanu, Dorian, and Axel Graeser; "Generation and Rendering of a Virtual Welding Seam in an Augmented Reality Training Environment," Proceedings of the Sixth IASTED International Conference on Visualization, Imaging, and Image Processing, Aug. 28-30, 2006, Palma de Mallorca, Spain, ED. J.J. Villaneuva, ACTA Press, 2006.

Aiteanu, Dorin, and Axel Graser, "Computer-Aided Manual Welding Using an Augmented Reality Supervisor," Sheet Metal Welding Conference XII, Livoinia, MI, May 9-12, 2006, pp. 1-14.

Aiteanu, Dorin, et al., "A Step Forward in Manual Welding: Demonstration of Augmented Reality Helmet," Institute of Automation, University of Bremen, Germany, 2003.

American Welding Society's Virtual Welding Trailer to Debut at FABTECH Careers in Welding Trailer Appeals to New Generation of Welders, Miami, Florida, Nov. 3, 2011.

American Welding Society Forms: typical Procedure Qualification Record and Welding Procedure Specification forms.

ArcSentry Weld Monitoring System, Version 3, Users Manual, Native American Technologies, Golden, CO, Dec. 10, 1999.

ARVIKA Forum Vorstellung Projeckt PAARA, BMW Group Virtual Reality Center, Nuernberg, 2003.

Ascension Technology Corporation: Tracking 3D Worlds: http://ascension-tech.com/, Dec. 1996.

Barckhoff, J.R.; "Total Welding Managemet," American Welding Society, 2005.

Bender Shipbuilding and Repair, Co., "Virtual Welding—A Low Cost Virtual Reality Welder Training System", Technical Proposal, Jan. 23, 2008.

(56) References Cited

OTHER PUBLICATIONS

Byrd, Alex Preston, "Identifying the effects of human factors and training methods on a weld training program" (2014). Graduate Theses and Dissertations. Paper 13991.
Central Welding Supply http://www.welders-direct.com/ Feb. 29, 2000.
Choquet, Claude, ARC$_+$: Today's Virtual Reality Solution for Welders, Jun. 1, 2008.
Choquet, Claude, ARC$_+$ & ARC PC Welding Simulators: Teach Welders with Virtual Interactive 3D Technologies; Jul. 2010.
Cybernetics: Enhancing Human Performance found in the DTIC Review dated Mar. 2001, p. 186/19. See http://www.dtic.mil/dtic/tr/fulltext/u2/a385219.pdf.
Dixon, Kevin et al.; "Gesture-based Programming for Robotic Arc Welding," Carnegie Mellon University, Dec. 6, 2002.
Echtler, Florian, Fabian Stuurm, Kay Kindermann, Gudrun Klinker, Joachim Stilla, Jorn Trilk, Hesam Najafi, "The Intelligent Welding Gun: Augmented Reality for Experimental Vehicle Construction," Virtual and Augmented Reality Applications in Manufacturing, Ong S.K and Nee A.Y.C., eds., Springer Verlag, 2003, pp. 1-27.
Evaluating Two Novel Tactile Feedback Devices, by Thomas Hulin, Phillipp Kremer, Robert Scheibe, Simon Schaetzle and Carsten Preusche presented at the 4th International Conference on Enactive Interfaces, Grenoble, France, Nov. 19-22, 2007.
EWI, "EWI ArcCheck," marketing brochure, Columbus, Ohio.
EWI, "EWI SkillBuilder," marketing brochure, Columbus, Ohio.
Fast, Kenneth, Jerry Jones, and Valerie Rhoades; "Virtual Welding—A Low Cost Virtual Reality Welder Training System Phase II," National Shipbuilding Research Program (NSRP), NSRP ASE Technology Investment Agreement No. 2010-357, Feb. 29, 2012, http://www.nsrp.org/3-RA-Panel_Final_Reports/FY08_Virtual_Welder_Final_Report.pdf.
Fast et al., Virtual Training for Welding, Proceedings of the Third IEEE and ACM International Symposium on Mixed and Augmented Reality (ISMAR 2004); 0-7695-2191-6/04; 2004.
Fite-Georgel, Pierre; "Is there a Reality in Industrial Augmented Reality?" 10th IEEE International Symposium on Mixed and Augmented Reality (ISMAR), 2011.
Fridenfalk et al., Design and Validation of a Universal 6D Seam Tracking System in Robotic Welding Based on Laser Scanning, Industrial Robotics: Programming, Simulation, and Application, ISBN 3-86611-286-6, pp. 702, ARS/pIV, Germany, Dec. 2006, edited by Kin Huat.
Fronius "The Ghost": http://www.fronius.com/cps/rde/xchg/SID-3202EAB7-AE082518/fronius_interational/hs.xsl/79_15490_ENG_HTML.htm; 2006.
Fronius International GmbH—Focus on Welding—Fronius Virtual Welding; http://www.fronius.com/cps/rde/xchg/SID-99869147-0110E322/fronius_intenational/hs.xsl/79_15490_ENG_HML.htm; 2006.
Fronius Perfect Welding; 06,3082, EN v01 2010 aw05; Virtual Welding—The training method of the future; Feb. 20, 2012.
ftp://www.hitl.washington.edu/pub/scivw/publications/IDS-pdf/HAPTIC1.PDF, (University of Washington): Table 11, Tactile Feedback Actuator Technologies, p. 119, below the table is a. Based on Hasser (1995, 1996).
GAWDA—Welding & Gases Today Online GAWDA Media Blog; Will Games Turn Welding into a Virtual Market? Friday, Dec. 2, 2011; http://www.weldingandgasestoday.org/blogs/Devin-OToole/index.php/ta.
Gundersen, O., et al. "The Use of an Integrated Multiple Neural Network Structure for Simultaneous Prediction of Weld Shape, Mechanical Properties, and Distortion in 6063-T6 and 6082-T6 Aluminum Assemblies", Mathematical Modelling of Weld Phenomena, vol. 5, Maney Publishing, 2001.
Haptic Feedback for Virtual Reality by Grigore C. Burdea dated 1996.
Hemez, Francois M., Scott W. Doebling, "Uncertainty, Validation of Computer Models an the Myth of Numerical Predictability," Engineering Analysis Group (ESA-EA), Los Alamos National Laboratory, dated 2004.
Hillers, B, and Axel Graeser, "Direct welding arc observation withouth harsh flicker," FABTECH International and AWS Welding Show, 2007.
Hillers, B, and Axel Graeser, "Real time Arc-Welding Video Observation System," 62nd International Conference of IIW, Jul. 12-17, 2009, Singapore, 2009.
Hillers, B., et al.; "TEREBES: Welding Helmet with AR Capabilites," Institute of Automation, University of Bremen, and Institute of Industrial Engineering and Ergonomics, RWTH Aachen Universty, 2004.
Hillers, Bernd, Dorin Aiteanu, Axel Graser, "Augmented Reality—Helmet for the Manual Welding Process," Virtual and Augmented Reality Applications in Manufacturing, Institute of Automation, Universtity of Bremen, 2004.
Himperich, Frederick, "Applications in Augmented Reality in the Automotive Industry," Fachgebiet Augmented Reality, Department of Informatics, Jul. 4, 2007, p. 1-21.
http://www.123arc.com "Simulation and Certification"; 2000.
Image from Sim Welder.com—R-V's Welder Training Goes Virtual, www.rvii.com/PDF/simwelder.pdf; Jan. 2010.
IMPACT Spring 2012 vol. 12, No. 2, Undergraduate Research in Information Technology Engineering, University of Virginia School of Engineering & Applied Science; 2012.
Impact Welding: miscellaneous examples from current and archived website, trade shows, etc. See, e.g., http://www.impactwelding.com.
Integrated Microelectromechanical Gyrosopes; Journal of Aerospace Engineering, Apr. 2003 pp. 65-75 (p. 65) by Huikai Xie and Garry K. Fedder.
International Search Report for PCT application No. PCT/US2015/04234, dated Nov. 27, 2015, 14 pgs.
International Search Report for PCT application No. PCT/US2009/045436, dated Nov. 9, 2009, 3 pgs.
International Search Report for PCT application No. PCT/US2012/050059 dated Nov. 27, 2012, 16 pgs.
International Search Report for PCT application No. PCT/US2013/038371 dated Jul. 31, 2013, 8 pgs.
International Search Report for PCT application No. PCT/US2013/066037 dated Mar. 11, 2014, 10 pgs.
International Search Report for PCT application No. PCT/US2013/066040 dated Mar. 11, 2014, 12 pgs.
International Search Report for PCT application No. PCT/US2014/018107, dated Jun. 2, 2014, 3 pgs.
International Search Report for PCT application No. PCT/US2014/018109, dated Jun. 2, 2014, 4 pgs.
International Search Report for PCT application No. PCT/US2014/018113, dated Jun. 2, 2014, 3 pgs.
International Search Report from PCT application No. PCT/US2014/018114, dated Jun. 2, 2014, 4 pgs.
International Search Report from PCT application No. PCT/US2014/065498, dated May 11, 2015, 13 pgs.
International Search Report from PCT application No. PCT/US2014/065506, dated Jun. 26, 2015, 16 pgs.
International Search Report from PCT application No. PCT/US2014/065512, dated Jun. 8, 2015, 17 pgs.
International Search Report from PCT application No. PCT/US2014/065525, dated Jul. 23, 2015, 16 pgs.
International Search Report from PCT application No. PCT/US2014/067951, dated Feb. 24, 2015, 10 pgs.
International Search Report from PCT application No. PCT/US2015-058667, dated Feb. 5, 2016, 14 pgs.
International Search Report from PCT application No. PCT/US2015/028939, dated Oct. 14, 2015, 13 pgs.
International Search Report from PCT application No. PCT/US2015/037410, dated Nov. 6, 2015, 10 pgs.
International Search Report from PCT application No. PCT/US2015/037439, dated Nov. 3, 2015, 12 pgs.
International Search Report from PCT application No. PCT/US2015/037440, dated Nov. 3, 2015, 12 pgs.
International Search Report from PCT application No. PCT/US2015/039680, dated Sep. 23, 2015, 12 pgs.
International Search Report from PCT application No. PCT/US2015/041462, dated Dec. 4, 2015, 14 pgs.

(56) References Cited

OTHER PUBLICATIONS

International Search Report from PCT application No. PCT/US2015/043370, dated Dec. 4, 2015, 12 pgs.
International Search Report from PCT application No. PCT/US2015/058666, dated Feb. 1, 2016, 11 pgs.
Jo et al., Visualization of Virtual Weld Beads, VRST 2009, Kyoto, Japan, Nov. 18-20, 2009; Electronics and Telecommunications Research Institute (ETRI) ACM 978-1 60558-869-8/09/0011.
Kiwinakiful; Holographic TV coming 2012 (as seen on BBC); http://www.youtube.com/watch?v=Ux6aD6vE9sk&feature=related, Jul. 2, 2011.
Kooima, Robert; Kinect +3D TV=Virtual Reality; http://www.youtube.com/watch?v=2MX1RinEXUM&feature=related, Feb. 26, 2011.
Leap Motion; https://www.leapmotion.com/, May 2012.
Lincoln Electric VRTEX Virtual Reality Arc Welding Trainer; http://www.lincolnelectric.com/en-us/equipment/training-equipment/pages/vrtex360.aspx; 1999.
MacCormick, John; How does the Kinect work?; http://users.dickinson.edu/~jmac/selected-talks/kinect.pdf, Dec. 1, 2011.
NAMeS, Native American Technologies Weld Measuring Software, Users Guide, 2000.
National Science Foundation—Where Discoveries Begin—Science and Engineering's Most Powerful Statements Are Not Made From Words Alone—Entry Details for NSF International Science & Engineering Visualization Challenge, Public Voting ended on Mar. 9, 2012; Velu the welder by Muralitharan Vengadasalam—Sep. 30, 2011; https://nsf-scivis.skild.com/skild2/NationalScienceFoundation/viewEntryDetail.action?pid.
Native American Technologies, "ArcDirector Weld Controller" web page, http://web.archive.org/web/20020608125127/http://www.natech-inc.com/arcdirector/index.html, published Jun. 8, 2002.
Native American Technologies, "ArcSentry Weld Quality Monitoring System" web page, http://web.archive.org/web/20020608124903/http://www.natech-inc.com/arcsentry1/index.html, published Jun. 8, 2002.
Native American Technologies, "Official NAMeS Web Site" web page, http://web.archive.org/web/20020903210256/http://www.natech-inc.com/names/names.html, published Sep. 3, 2002.
Native American Technologies, "P/NA.3 Process Modelling and Optimization" web pages, http://web.archive.org/web/20020608125619/http://www.natech-inc.com/pna3/index.html, published Jun. 8, 2002.
Native American Technologies, "Process Improvement Products" web page, http://web.archive.org/web/20020608050736/http://www.natech-inc.com/products.html, published Jun. 8, 2002.
Natural Point, Trackir; http://www.naturalpoint.com/trackir/, Dec. 2003.
Numerical Simulation F Arc Welding Process and its Application Dissertation for Ohio State University by Min Hyun Cho, M.S. 2006: See Internet as this document is security protected) ohttps://etd.ohiolink.edu/ap:0:0:APPLICATION_PROCESS=DOWN-LOAD_ETD_SUB_DOC_ACCNUM:::F1501_ID:osu1155741113, attachment.
NZ Manufacturer Game promotes welding trade careers; http://nzmanufacturer.co.nz/2011/11/gme-promotes-welding-trade-careers/ . . . Compentenz Industry Training; www.competenz.org.nz; Game promotes welding trade careers, Nov. 7, 2011.
OptiTrack: Motion Capture Systems: http://www.naturalpoint.com/optitrack/, Mar. 2005.
Penrod, Matt; "New Welder Training Tools," EWI PowerPoint presentation, 2008.
PhaseSpace: Optical Motion Capture: http://phasespace.com/, 2009.
Playstation; Move Motion Controller: http://us.playstation.com/ps3/playstation-move/, Mar. 2010.
Polhemus: Innovation in Motion: http://polhemus.com/?page=researchandtechnology, 1992.
Porter, Nancy C., Edison Welding Institute; J. Allan Cote, General Dynamics Electrict Boat; Timothy D. Gifford, VRSim; and Wim Lam, FCS Controls—Virtual Reality Welder Training—Project No.

S1051 Navy Man Tech Program; Project Review for Ship Tech 2005,—Mar. 1, 2005, Biloxi, MS, http://www.nsrp.org/6-Presentations/WD/Virtual_Welder.pdf.
Porter, Nancy C., Edison Welding Institute; J.Allan Cote, General Dynamics Electric Boat; Timoty D. Gifford, VRSim; and Wim Lam, FCS Controls—Virtual Reality Welder Training—Session 5; Joining Technologies for Naval Applications; 2007.
Porter et al., EWI-CRP Summary Report SR0512, Jul. 2005—Virtual Reality Welder Training.
Quebec International, May 28, 2008 "Video Game" Technology to Fill Growing Need; http://www.mri.gouv.qc.ca/portail/_scripts/actualities/viewnew.sap?NewID=5516.
Ryu, Jonghyun, Jaehoon Jung, Seojoon Kim, and Seungmoon Choi, "Perceptually Transparent Vibration Rendering Using a Vibration Motor for Haptic Interaction," 16 IEEE International Conference on Robot & Human Interactive Communication, Jeju, Korea, Aug. 26-29, 2007.
Sandor, Christian, Gudrun Klinker, "PAARTI: Development of an Intelligent Welding Gun for BMW," PIA 2003, Tokyo, Japan, Technical University of Munich Department of Informatics, Oct. 7, 2003.
Sandor, Christian, Gudrun Klinker; "Lessons Learned in Designing Ubiquitous Augmented Reality User Interfaces," Emerging Technologies of Augmented Reality Interfaces, Eds. Haller, M, Billinghurst, M., and Thomas, B., Idea Group Inc., 2006.
ShotOfFuel; Wii Head Tracking for 3D, http://www.youtube.com/watch?v=1x5ffF-0Wr4, Mar. 19, 2008.
Sternowski, Andreas; "Handheld Welding Torch with Position Detection," Patente Fonds, Patent Portfolio, Sep. 21, 2011.
Stone, R. T., K. Watts, and P. Zhong, "Virtual Reality Integrated Welder Training, Welding Research," Welding Journal, vol. 90, Jul. 2011, pp. 136-s-141-s, https://app.aws.org/wj/supplement/wj201107_s136.pdf.
TCS News & Events: Press Release: TCS wins the "People Choice" award from National Science Foundation, USA, pp. 1-6; Press Release May 21, 2012; http://www.tsc.com/news_events/press_releases/Pages/TCS_People_Choice_award_Natio.
teachWELD: Welding Simulator/Hands-On Learning for Welding: http://realityworks.com/products/teachweld-welding-simulator; 2012.
Terebes; miscellaneous examples from http://www.terebes.uni-bremen.de.
The Rutgers Master II—New Design Force-Feedback Glove by Mourad Bouzit, Member, IEEE, Grigore Burdea, Senior Member, IEEE, George Popescu, Member, IEEE, and Rares Bolan, Student Member, found in IEEE/ASME Transactions on Mechatronics, vol. 7, No. 2, Jun. 2002.
thefabricator.com—Arc Welding Article; Heston, Tim, Virtual welding—Training in a virtual environment gives welding students a leg up—Mar. 11, 2008.
Tschurner, Petra, Hillers, Bernd, and Graeser, Axel; "A Concept for the Application of Augmented Realty in Manual Gas Metal Arc Welding," Proceedings of the International Symposium on Mixed and Augmented Reality, 2002.
Vicon: Motion Capture Systems: http://vicon.com/, Dec. 1998.
Virtual Reality Training Manual Module 1—Training Overview—A Guide for Gas Metal Arc Welding—EWI 2006.
Welding Journal, American Welding Society, Nov. 2007, https://app.aws.org/wj/2007/11/WJ_2007_11.pdf.
White, S., et al., "Low-Cost Simulated MIG Welding for Advancement in Technical Training," Virtual Reality, 15, 1, 69-81, Mar. 2011. ISSN:13594338 [Retrieved from EBSCOhost, Jun. 15, 2015].
"SOLDAMATIC: Augmented Training Technology for Welding," Seabery Augmented Training Technology, Seabery Soluciones, 2011.
Hashimoto, Nobuyoshi et al., "Training System for Manual Arc Welding by Using Mixed Reality: Reduction of Position-Perception Error of Electrode Tip," Journal of the Japan Society for Precision Engineering, vol. 72, pp. 249-253, 2006.
International Search Report for PCT application No. PCT/US2015/058563, dated Jan. 29, 2016, 13 pgs.
International Search Report from PCT application No. PCT/US2014/018103, dated Jun. 30, 2014, 13 pgs.
International Search Report from PCT application No. PCT/US2015/058567, dated May 6, 2016, 15 pgs.

(56) References Cited

OTHER PUBLICATIONS

International Search Report from PCT application No. PCT/US2015/058569, dated Feb. 10, 2016, 12 pgs.
International Search Report from PCT application No. PCT/US2015/058660, dated Feb. 2, 2016, 14 pgs.
International Search Report from PCT application No. PCT/US2015/058664, dated Apr. 25, 2016, 17 pgs.
International Search Report from PCT application No. PCT/US2016/023612, dated Jul. 18, 2016, 11 pgs.
Kobayashi, Kazuhiko et al., "Modified Training System for Manual Arc Welding by Using Mixed Reality and Investigation of Its Effectiveness," Journal of the Japan Society for Precision Engineering, vol. 70, pp. 941-945, 2004.
Kobayashi, Kazuhiko et al., "Simulator of Manual Metal Arc Welding with Haptic Display," Chiba University, ICAT 2001, Dec. 2001.
Kobayashi, Kazuhiko et al., "Skill Training System of Manual Arc Welding by Means of Face-Shield HMD and Virtual Electrode," Chiba University, Japan, R. Nakatsu et al. (eds.), Entertainment Computing, Springer Science +Business Media, New York, 2003.
VRTEX 360 Operator's Manual, Lincoln Electric, Oct. 2012.
VRTEX 360, Lincoln Electric, Dec. 2009.
Canadian Office Action Appln. No. 2,959,374 dated Dec. 11, 2017 (5 pages).
Canadian Office Action Appln No. 2,959,374 dated Sep. 30, 2019.
Canadian Office Action Appln. No. 2,958,203 dated Oct. 4, 2019 (5 pages).

* cited by examiner

REMOTE POWER SUPPLY PARAMETER ADJUSTMENT

BACKGROUND

The invention relates generally to welding systems and, more particularly, to sensing systems for displaying and changing power supply settings remotely.

Welding is a process that has become ubiquitous in various industries for a variety of types of applications. For example, welding is often performed in applications such as shipbuilding, aircraft repair, construction, and so forth. The welding systems often include power supplies that may generate power for consumption during the welding process. However, these power supplies may often be remote from a work area, thereby causing delays if a user changes settings of a power supply due to travel to and from the power supply to make the changes.

BRIEF DESCRIPTION

In a first embodiment, a welding-type system includes a helmet comprising. The helmet includes an electronic display configured to display a representation of a welding-type power supply and to display one or more indications of one or more parameters of the welding-type power supply. The helmet also includes a first inertial measurement unit configured to detect movement of the helmet. Furthermore, the welding system includes a processing system communicatively coupled to the first inertial measurement unit and configured to adjust at least one parameter of the one or more parameters based at least in part on the movement of helmet.

In another embodiment, a method includes displaying a representation of a welding power supply including one or more parameters of a welding-type power supply on an electronic display of a helmet. The method also includes receiving a command remote from the welding-type power supply, wherein the command is configured to set a parameter of the one or more parameters. Furthermore, the method includes adjusting the parameter, at the welding-type power supply, based at least in part on the command.

In a further embodiment, a welding-type system includes a helmet. The helmet includes an electronic display configured to display a representation of the welding-type power supply and to display one or more indications of one or more parameter of the welding-type power supply. The helmet also includes an audible command unit configured to receive audible commands. Additionally, the system includes a processing system communicatively coupled to the audible command unit and configured to adjust at least one parameter of the one or more parameters based at least in part on audible commands.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As will be described in detail below, provided herein are systems and methods for viewing and controlling power sources remotely. By viewing and controlling the power sources remotely, an operator may weld a workpiece with desired parameters without walking away from the workpiece. In other embodiments, a welding operator may control the parameters of a weld without spending valuable weld time traveling to the power supply to view and control the power supply. Thus, the operator may weld more quickly and efficiently with desired parameters. Furthermore, the operator may confirm welding parameters prior to a weld without substantial delay that may be required when having to walk back to the power source to change welding parameters.

Figure 1:
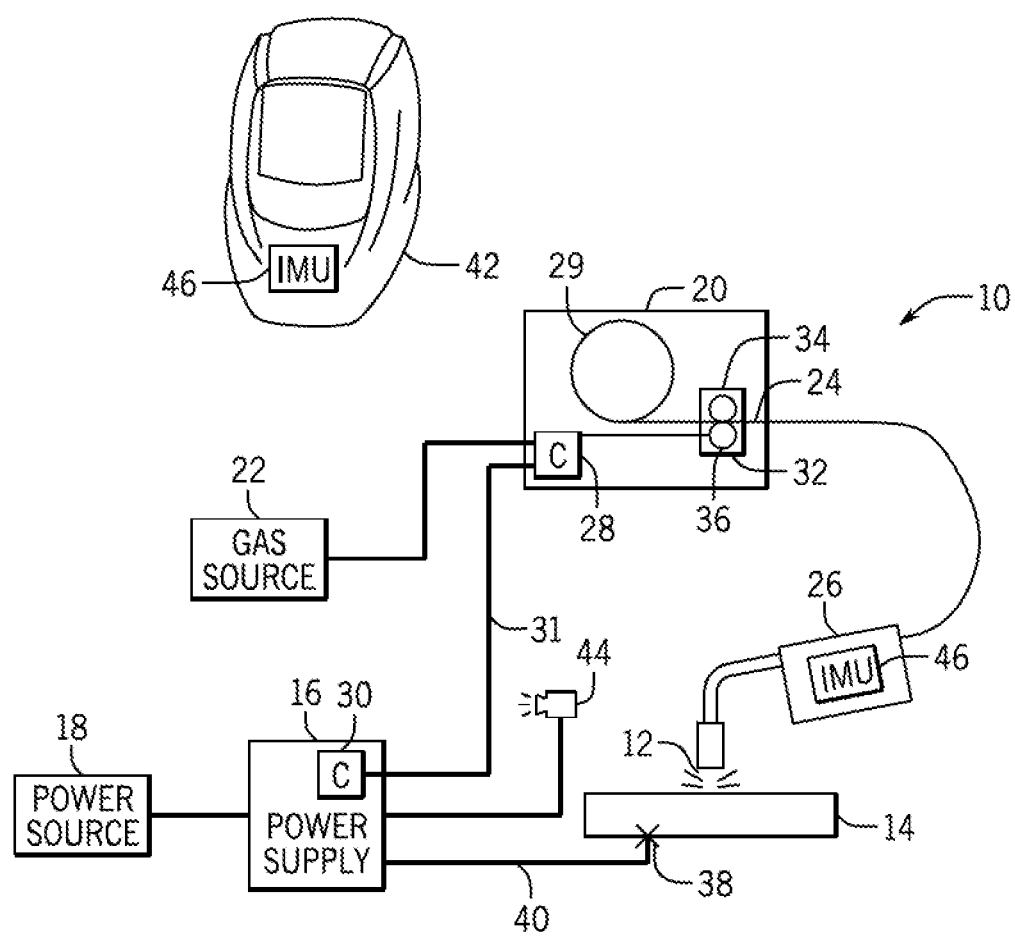
FIG. 1 is a block diagram of an embodiment of a welding system utilizing a welding helmet.

Turning now to the figures, FIG. 1 is a block diagram of an embodiment of a welding system 10 in accordance with the present techniques. The welding system 10 is designed to produce a welding arc 12 with a workpiece 14 (e.g., pipe). The welding arc 12 may be generated by any type of welding system or process, and may be oriented in any desired manner. For example, such welding systems may include gas metal arc welding (GMAW) systems, and may utilize various programmed waveforms and settings. The welding system 10 includes a power supply 16 that will typically be coupled to a power source 18, such as a power grid, an engine, or a combination thereof (e.g., hybrid power). Other power sources may, of course, be utilized including generators and so forth. In the illustrated embodiment, a wire feeder 20 is coupled to a gas source 22 and the power supply 16, and supplies welding wire 24 to a welding torch 26. The welding torch 26 is configured to generate the welding arc 12 between the welding torch 26 and the workpiece 14. The welding wire 24 is fed through the welding torch 26 to the welding arc 12, melted by the welding arc 12, and deposited on the workpiece 14.

The wire feeder 20 will typically include wire feeder control circuitry 28, which regulates the feed of the welding wire 24 from a spool 29 and also may command the output of the power supply 16, among other things. Similarly, the power supply 16 may include power supply control circuitry 30 for monitoring and controlling certain welding parameters and arc-starting parameters. In certain embodiments, the wire feeder control circuitry 28 or the power supply control circuitry 30 may include software, hardware, or a combination thereof. For example, in certain embodiments, the wire feeder control circuitry 28 and/or the power supply control circuitry 30 may include a processor and a tangible, non-transitory, computer-readable memory configured to store instructions to be executed by the processor. In some embodiments, the wire feeder control circuitry 28 may communicate with the power supply control circuitry 30 through a weld cable 31 that is also used to provide power to the wire feeder 20. In some embodiments, the power supply control circuitry 30 may be enclosed in a housing of the power supply 16. In some embodiments, at least some of the processing may be performed by another processor (e.g., processor in the helmet).

The spool 29 of the wire feeder 20 will contain a length of welding wire 24 that is consumed during the welding operation. The welding wire 24 is advanced by a wire drive assembly 32, typically through the use of an electric motor used to drive wheels 34 and 36 used to advance the welding wire 24. In some embodiments, the electric motor is under control of the control circuitry 28. In addition, the workpiece 14 may be coupled to the power supply 16 by a clamp 38 connected to a work cable 40 to complete an electrical circuit when the welding arc 12 is established between the welding torch 26 and the workpiece 14.

Placement of the welding torch 26 at a location proximate to the workpiece 14 allows electrical current, which is provided by the power supply 16 and routed to the welding torch 26, to arc from the welding torch 26 to the workpiece 14. As described above, this arcing completes an electrical circuit that includes the power supply 16, the welding torch 26, the workpiece 14, and the work cable 40. Particularly, in operation, electrical current passes from the power supply 16, to the welding torch 26, to the workpiece 14, which is typically connected back to the power supply 16 via the work cable 40. The arc generates a relatively large amount of heat that causes part of the workpiece 14 and the filler metal of the welding wire 24 to transition to a molten state that fuses the materials, forming the weld.

In certain embodiments, to shield the weld area from being oxidized or contaminated during welding, to enhance arc performance, and to improve the resulting weld, the welding system 10 may also feed an inert shielding gas to the welding torch 26 from the gas source 22. It is worth noting, however, that a variety of shielding materials for protecting the weld location may be employed in addition to, or in place of, the inert shielding gas, including active gases and particulate solids. Moreover, in other welding processes, such gases may not be used, while the techniques disclosed herein are equally applicable.

Although FIG. 1 illustrates a GMAW system, the presently disclosed techniques may be similarly applied across other types of welding systems, including gas tungsten arc welding (GTAW) systems and shielded metal arc welding (SMAW) systems, among others. Accordingly, embodiments of the sensor-based power supply controls may be utilized with welding systems that include the wire feeder 20 and gas source 22 or with systems that do not include a wire feeder 20 and/or a gas source 22 (e.g., embodiments where the welding torch 26 is directly coupled to the power supply 16), depending on implementation-specific considerations.

Presently disclosed embodiments are directed to remote power supply monitoring, viewing, and control. In some embodiments, data related to the power supply 16 may be sent to a welding helmet 42 and presented to an operator wearing the helmet 42. In some embodiments, the data may be presented visually or audibly to the operator. Furthermore, visual data may include images of the power supply 16 taken by one or more cameras 44 showing settings of the power supply 16. In certain embodiments, the operator may modify parameters remotely based on the presented parameters. For example, in certain embodiments, the operator may speak audible commands into the helmet 42 or issue commands that are detected by the helmet 42 or an inertial measurement unit (IMU) 46 in the welding torch 26, the helmet 42, gloves, and/or other suitable locations. In some embodiments, the commands may be detected via a camera and other sensory apparatus in a work area where welding is being performed. Additionally or alternatively, some commands may be received via an electronic device, such as a computer, smart phone, tablet, or other electronic device capable of receiving input from the operator.

In certain embodiments, the IMU 46 may include an accelerometer, a magnetometer, a rate sensor (e.g., a gyroscope sensor), or other sensors capable of measuring movements of the operator. As used herein, a rate sensor may include MEMs based sensors or any device which provides a signal output indicating an angular rate of change within a three dimensional frame of reference. For example, a single axis rate sensor would indicate a rate of change about a single coordinate normal to the sensor's reference plane. The accelerometer may include a single triaxial accelerometer capable of measuring dynamic motion, such as weld weaving. In other embodiments, the accelerometer may include one or more orientation sensors to determine a change of welding torch 26 orientations in one or more dimensions. For example, a two-dimensional position may be calculated with respect to a plane parallel to a direction of gravity based on two accelerometers. In some embodiments, the rate sensor may include one or more rate sensors, such as a single triaxial rate sensor. The power supply control circuitry 30 and/or the wire feeder control circuitry 28 may use the rate sensor to supplement data from the accelerometer to measure smaller or finer movements. In certain embodiments, the magnetometer may include one or more magnetometer sensors, such as a single triaxial magnetometer. The power supply control circuitry 30 and/or the wire feeder control circuitry 28 may use the magnetometer to determine changes in magnetic fields such as movement of the welding torch 26 or other objects in the weld area. Using one or more sensor types in the IMU 46, the welding system 10, via the control circuitry 30 and/or the wire feeder control circuitry 28, may receive detected motion data that may control the power supply 16.

Figure 2:
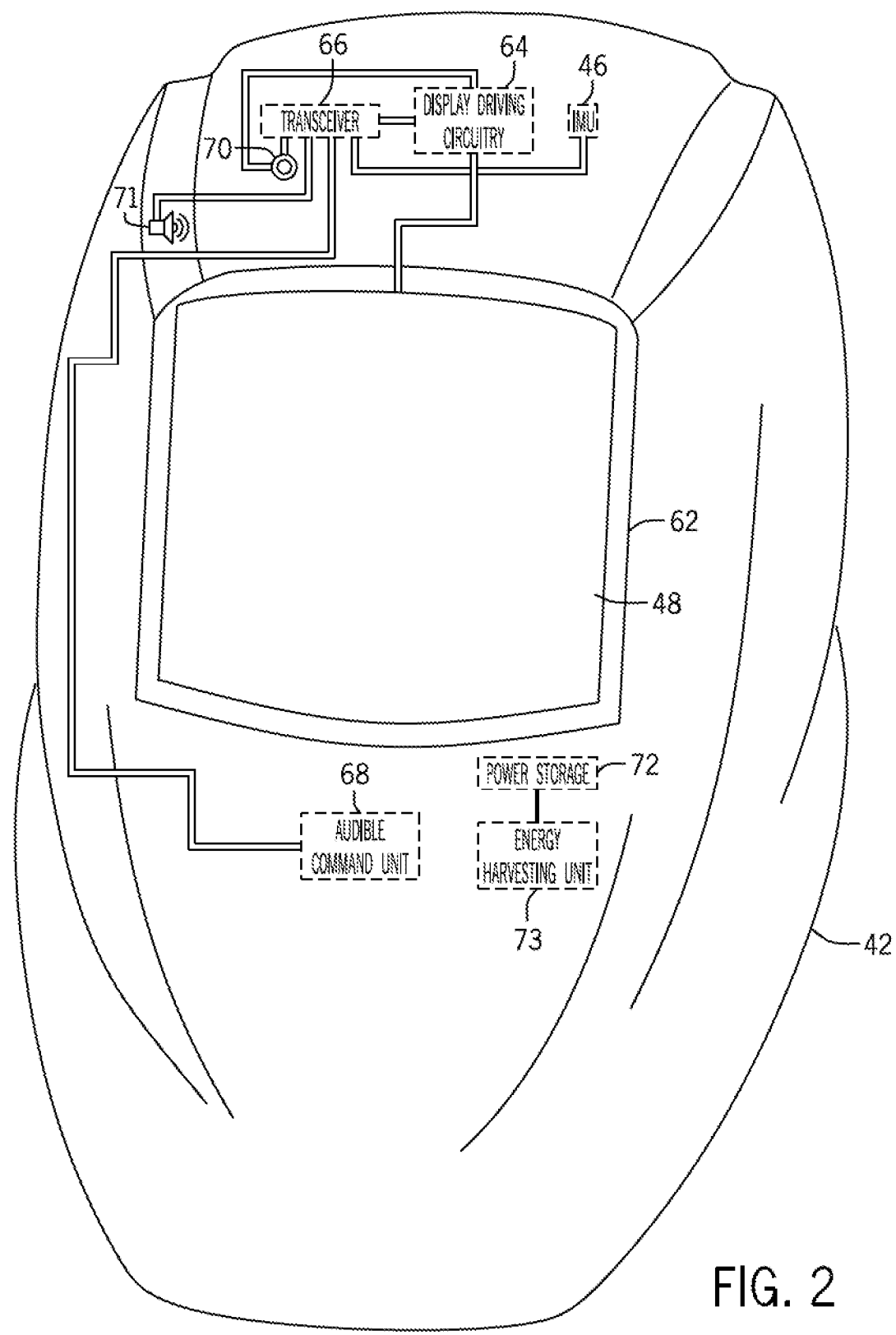
FIG. 2 is a block diagram of an embodiment of the welding helmet of FIG. 1 illustrating an electronic display.

Using data from one or more of the sensors, the power supply control circuitry 30 and/or the wire feeder control circuitry 28 may control the power supply 16 to change one or more parameters as desired by an operator without the operator physically walking to the power supply 16. As previously discussed, the welding helmet 42 may display the parameters to be controlled, the power supply 16, or a representation of the power supply 16 via a display, such as the display 48 included inside the welding helmet 42 of FIG. 2. In certain embodiments, the display 48 may include an electronic screen used to replace a viewing area of traditional welding helmets. For example, in some embodiments, auto-darkening glass of a welding helmet may be removed and replaced with the display 48. In certain embodiments, the display 48 may include two separate displays, each display capable of showing images independent from the other display. In such embodiments, the two displays may be used to show a stereoscopic view of various objects, such as the work area and/or the power supply 16.

Figure 3:
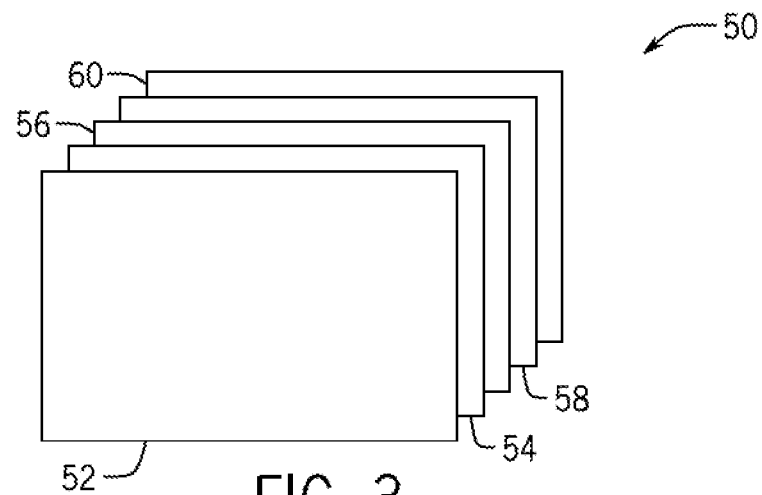
FIG. 3 is an exploded view of an embodiment of layers that may be included in the electronic display of FIG. 2.

In other embodiments, a clear display 48 may be layered onto glass of a welding helmet. FIG. 3 illustrates layers 50 of the display 48 that may be placed in the viewing area of the helmet 42. Although the layers 50 includes five layers, in some embodiments, additional layers may be included, some layers may be omitted, two or more layers may combined into a single layer, and/or some layers may be separable into multiple distinct layers (e.g., a polarizing layer, transistor layer, etc.). In other words, in some embodiments, the layers 50 may include 1, 2, 3, 4, 5, 6, or more layers. In the illustrated embodiment, the layers 50 include an inner transparent layer 52, a transparent display layer 54, an insulating layer 56, an autodarkening layer 58, and an outer transparent layer 60. The inner transparent layer 52 may protect the display layer 54 from contact and/or damage from contacting objects within the helmet 42 while enabling a user wearing the helmet 42 to see the images shown by the transparent display layer 54. For example, in some embodiments, the inner transparent layer 52 may include glass or a transparent plastic.

The transparent display layer 54 may include display circuitry that enables the user to see images created and intended to be displayed while still observing the user's actual surrounding area through the transparent display circuitry layer 54. For example, the transparent display layer 54 may include a transparent liquid crystal display (LCD), an organic light emitting diode (OLED) display, or other displays that enable an operator to see what is on the display layer 54 while still being able to see through the display layer 54. In some embodiments, the transparent display layer 54 may include a prism that reflects images projected to one or more parts of the prism. As discussed below, in some embodiments, the display layer 54 may only be capable of displaying images on a portion of the viewing area. However, in some embodiments, the display layer 54 may encompass the whole viewing area of the helmet 42.

In some embodiments, the layers 50 include an insulating layer 56 that separates the display layer 54 from the autodarkening layer 58 to block interference of operation of electronic components of the display layer 54 and/or the autodarkening layer 58 from other layers or each other. In some embodiments, the insulating layer 56 may include a substrate layer of the transparent display layer 54. The autodarkening layer 58 may include electrochromic, photochromic, thermochromic, suspended particle, micro-blind, or other autodarkening smart glass. In some embodiments, the display layer 54 and the autodarkening layers 58 may be combined into a single layer. For example, the liquid crystals of a transparent LCD may be used to darken incoming light by partially closing and/or displaying images using color filters on at least some of the liquid crystals. In some embodiments, the layers 50 may also include an outer transparent layer 60 that at least protects the other layers of the layers 50 from damage outside the helmet 42.

Returning to FIG. 2, in some embodiments, the display 48 may be coupled to the helmet 42 via a bevel 62 that houses display circuitry and couples the display 48 to display driving circuitry 64. In some embodiments, the display driving circuitry 64 may include row and column pixel controls for the display layer 54 or a projection device for projecting images onto a prism of the display layer 54. The helmet 42 may also include a transceiver 66 that receives image data from one or more remote devices (e.g., camera 44) and returns information to the remote device. In certain embodiments, the transceiver 66 may include a wireless transceiver, such as a ZigBee, 802.15.4, Bluetooth, 802.11, and/or other wireless transceiver. Additionally or alternatively, the transceiver 66 may include a wired connection transceiver. In some embodiments, the transceiver 66 may be a uni-direction receiver that receives video data. However, in some embodiments, the transceiver 66 may send commands from the helmet 42 back to a control unit, such as the power supply control circuitry 30 and/or the wire feeder control circuitry 28. For example, the transceiver 66 may send motion commands detected by the IMU 46, auditory commands (e.g., vocal commands) detected by an audible command unit 68, and/or visual commands detected by camera(s) 70. In some embodiments, at least in some modes, the transceiver 66 may not receive images for display via the display 42 because the display 42 merely displays images captured from the camera(s) 70 rather than receiving images from a remote location.

In some embodiments, the helmet 42 may include a speaker 71 used to convey auditory information to the user. For example, the speaker 71 may receive audible signals from the power supply control circuitry 30 and/or the wire feeder control circuitry 28 via the transceiver 66 indicating a power supply parameter, receipt of a command from the user, a type of power supply 16, or other information useful in informing a user of changes to operating parameters and generate an audible indication of such information to the user.

The helmet 42 may also include a power storage 72 that stores power for use by the transceiver 66, display 48, display driving circuitry 64, IMU 46, display 48, speaker 71, audible command unit 68, and/or additional circuitry. The power storage 72 may include any suitable unit for storing power that may be used to power electrical components, such as capacitors or batteries formed from galvanic cells, electrolytic cells, fuel cells, flow cells, and/or voltaic piles. The power storage 72 may store energy received from an energy harvesting unit 73 and/or external power source (e.g., AC line power). The energy harvesting unit 73 derives energy from around the user to provide power to the power storage 72. For example, the energy harvesting unit 73 may include kinetic energy captures using electromagnetic generators, photovoltaic cells, thermoelectric generators, antennas to recover radio wave energy, or other items capable of converting energy into a form (e.g., chemical or electrical) suitable for storage in the power storage 72.

Figure 4:
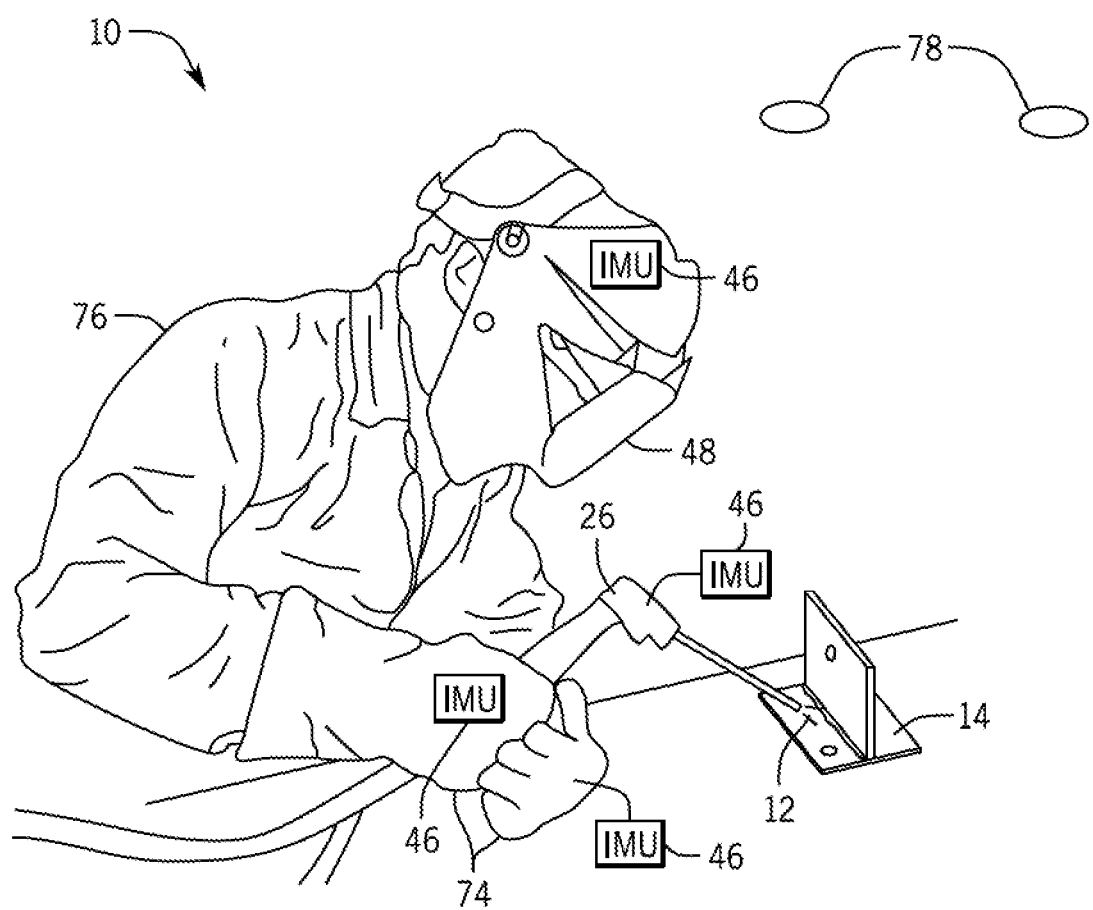
FIG. 4 is a perspective view of an embodiment of the welding system of FIG. 1 showing an inertial measurement unit.

FIG. 4 is a perspective view of an embodiment of the welding system 10 capable of monitoring a position of the welding helmet 42, welding torch 26, and/or gloves 74 to detect control commands from an operator. In the depicted welding system 10, an operator 76 is wearing the welding helmet 42 while welding. In certain embodiments, external helmet position detection sensors 78 are located near the operator 76 in a welding job area to aid the data from the IMUs 46 in assessing the position and orientation of the welding helmet 42, welding torch 26, and/or gloves 74.

It should be noted that the sensors 78 may include, or be replaced by, any method or device capable of detecting the position of the welding helmet 42. For example, the sensors 78 may include a stereo-vision camera or one or more mono-vision cameras located overhead to determine the location and orientation of the welding helmet 42. The cameras may be located on the welding helmet 42 (e.g., cameras 70) to locate the relative position of the helmet 42, welding torch 26, gloves 74, and/or capturing images of the work area for display via the display 48. The sensors 78 may include optical sensors for determining the position of the welding helmet 42, welding torch 26, and/or gloves 74 by determining a position of a predefined point, such as the workpiece 14. In some embodiments, the helmet 42 may include markings that reflect light or active visual markings that include infrared LEDs. In certain embodiments, the orientation of the helmet 42, welding torch 26, and/or gloves 74 in relation to each other, in relation to the workpiece 14, or in relation to the operator may be visually determined, for example, via helmet markings or geometric features detected by a plurality of camera imagers external to the welding helmet 42.

In still other embodiments, the sensors 78 may include a single optical sensor configured to detect structured light projected onto the welding helmet 42 from a light source external to the welding helmet 42. The light source may include a point source at a fixed location relative to the sensors 78. The light source may project a grid or other structured pattern toward the helmet 42, welding torch 26, and/or gloves 74. Wherever the pattern strikes the welding helmet 42 (or welding torch 26 or gloves 74), the light may produce a pattern indicative of the shape and distance of the welding helmet 42 (or welding torch 26 of gloves 74) from the sensors 78. As the light hits the welding helmet 42 (or welding torch 26 of gloves 74) from different angles, the projected grid may become distorted based on the contours of the welding helmet 42 (or welding torch 26 of gloves 74). The welding helmet 42 (or welding torch 26 of gloves 74) may be shaped such that the distorted grid may be utilized to identify a position, distance, and orientation of the welding helmet 42 (or welding torch 26 of gloves 74) via image processing of images acquired via the sensors 78. The structured light could include an array of points, circles, stripes, or any desirable collection of light patterns that can be recognizable.

Figure 5:
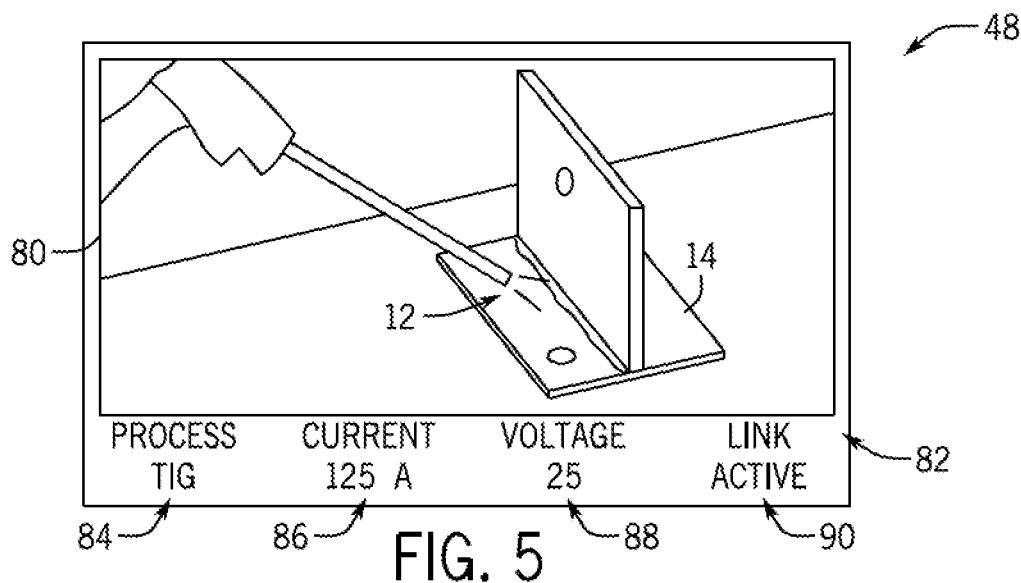
FIG. 5 is an embodiment of an image of a working view that may be displayed by the display of FIG. 2.
Figure 6:
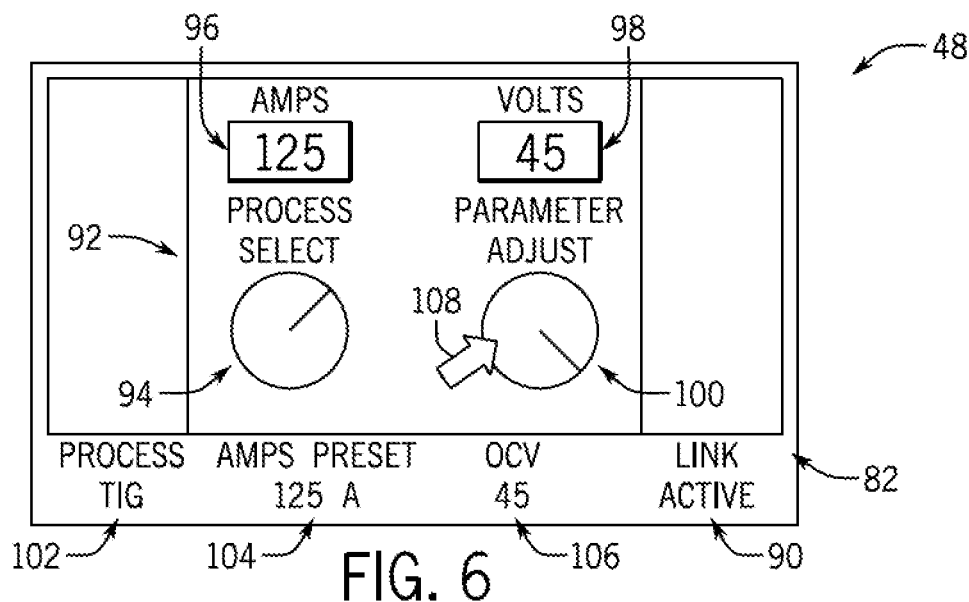
FIG. 6 is an embodiment of an image of a parameter adjustment view that may be displayed by the display of FIG. 2.

As previously discussed, the helmet 42 may display various parameters of the power supply 16. For example, FIG. 5 illustrates an image that might be presented to the user via the display 48. The helmet 42 may enable the user to view a workpiece 14 and a welding arc 12. As previously discussed, in some embodiments, the display 48 reproduces a working view 80 via image capturing (e.g., via one or more cameras 70). In certain embodiments, the display 48 may be at least partially transparent to enable the user to view the working view 80. In other embodiments, the display 48 may display captured images of the working view 80 via the camera(s) 70. In some embodiments, the display 48 may be horizontally bifurcated into two separate displays or may be horizontally partitioned into two viewing areas that enable the helmet 42 to present different images to each eye of the welder. For example, the left display or display area may be used to present an image stream from a left-side camera that a captures a perspective similar to that which would be viewed by a left eye. Similarly, the right display or display area may be used to present an image stream from a right-side camera that captures a perspective similar to that which would be viewed by a right eye. This stereoscopic viewing would allow the welder to see the working area more accurately to add depth perception and three-dimensional viewing to the display 48.

In certain embodiments, the display 48 may include a heads up display (HUD) 82 that informs the user of various parameters of the power supply 16 and/or the welding process being used. For example, the HUD 82 may include a process type indication 84, a current level indication 86, a voltage level indication 88, and a link indication 90, and/or other parameters that may be helpful for the operator to know for the welding process. The process type indication 84 indicates what type of welding process is currently being employed, such as tungsten inert gas (TIG) welding, metallic inert gas (MIG) welding, shielded metal arc welding (SMAW), gas metal arc welding (GMAW), or other suitable welding processes. The current level indication 86 indicates a current level for the welding process. Similarly, the voltage level indication 88 indicates a voltage level for the welding process. Furthermore, the link indication 90 indicates that a connection to the power supply 16 from the welding torch 26 is active or inactive. In some embodiments, the link indication 90 indicates that the HUD 82 is actively receiving data from the power supply 16 and that the currently displayed parameters are recently received from the power supply 16.

In some embodiments, while viewing the working view 80, the operator may initiate a power supply view in which the display 48 shows a power supply 92. In some embodiments, the power supply 92 may be a caricature or simplified view corresponding to a type matching the type of power supply 16. In some embodiments, the power supply 92 may be an image of the actual power supply 16 either previously saved or shown in substantially real time via the camera 44. In certain embodiments, the power supply 92 may include various information and manipulatables that may be found on the front of the power supply 16. For example, the power supply 92 may include a process selection dial 94, a current unit 96, a voltage unit 98, and a parameter adjust dial 100. The process selection dial 94 may be used to set what type of process is used for the weld process and indicated by the process indicator 102 of the HUD 82. Similarly, the current unit 96 may display a current level that may also be reflected in the current level indicator 104 of the HUD 82, and the voltage unit 98 may display a voltage level that may also be reflected in the voltage level indicator 106 of the HUD 82.

In the present embodiment, the voltage level indicator 106 indicates an open circuit voltage (OCV) that corresponds to a difference in electrical potential between two terminals of the power supply 16 when disconnected from an external circuit (e.g., circuit including the welding torch 26 and the workpiece 14). In some embodiments, the parameter adjust dial 100 may be used to adjust voltage, current, or other parameters of the power supply 16. Although the process selection dial 94 and the parameter adjust dial 100 are dials, in some embodiments, the dials 94, 100 may be replaced by any other manipulatable capable of receiving user input, such as arrows, number entry keyboards, and so forth. In some embodiments, the operator may manipulate one or more parameters using a cursor 108.

In certain embodiments, the cursor may be a box or other indicator that indicates which parameter is being changed. In some embodiments, the cursor may be moved using gestures (e.g., head movements up or down, head movements left or right, hand gestures up or down, hand gestures left or right) or vocal commands (e.g., "left"). In some embodiments, the hand gestures may include a horizontal swipe (e.g., left or right), a vertical swipe (e.g., up or down), a circular motion (e.g., clockwise or counterclockwise loop), a twist (e.g., clockwise or counterclockwise rotation of the torch 26), or other gestures that may be recognized by the sensors. In other words, the raw data generated by the sensors may be analyzed to determine when certain gestures are being performed by the operator. In some embodiments, the gestures may be analyzed by a preprocessor prior to communication to the power supply control circuitry 30 and/or the wire feeder control circuitry 28. In other embodiments, the power supply control circuitry 30 and/or the wire feeder control circuitry 28 may analyze raw data from the sensors to recognize the gestures. In some embodiments, the cursor 108 and manipulatables may be replaced with vocal commands (e.g., "amplitude increase by 5").

In some embodiments, the process selection dial 94 and/or the parameter adjust dial 100 may be omitted or collapsed with respective display portions. For example, functionality of the process selection dial 94 may be included into the process indicator 102. In some embodiments, the display portions (e.g., portions of the HUD 82) may be only manipulatable in one mode while locked in another mode. For example, a user may issue a voice command, such as "parameter adjustment mode," that initiates the parameter adjustment mode that allows the operator to modify power supply parameters remotely.

Although the foregoing discussion contemplates displaying power supply monitoring and manipulation via the welding helmet 42, in some embodiments, at least some of the display and or control of the power supply 16 may be performed via a smart device (e.g., a smart phone). For example, when a smart device is on the same network (e.g., WiFi) as the power supply 16, a control application may be employed to monitor and change parameters of the power supply 16.

Figure 7:
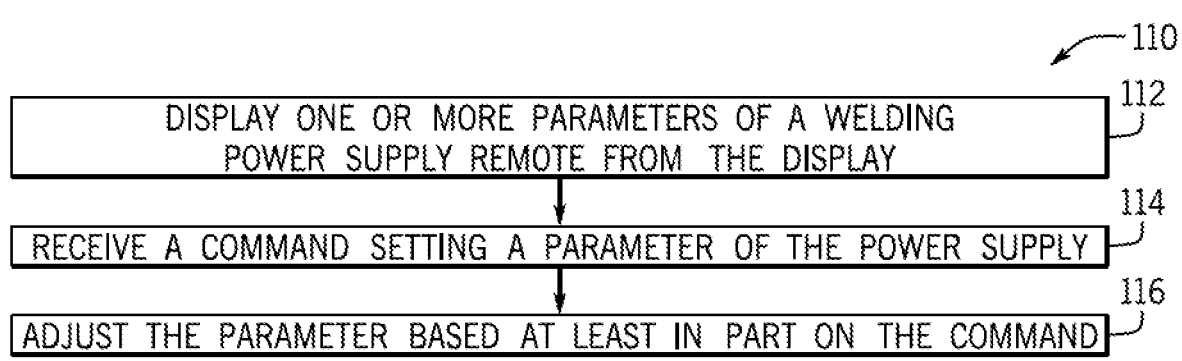
FIG. 7 is a flowchart diagram view of an embodiment of a process for adjusting parameters of the power supply of the welding system of FIG. 1.

FIG. 7 illustrates a process 110 that may be used to monitor and/or change parameters of the power supply 16 remotely. The process 110 includes displaying, via a smart device or a welding helmet, one or more parameters of a power supply 16 to a user remote from the power supply 16 (block 112). The process 110 also includes receiving commands from a user remote from a power supply 16 (block 114). For example, the commands may include gestures and/or audio commands from a user that is far away from a power supply 16 without direct sight of the power supply 16. Based on the commands, at least one parameter of the power supply 16 may be adjusted (block 116).

For instance, in certain embodiments, when a welding operator is in the middle of a weld, the operator's welding helmet 42 may display a HUD 82 showing parameters of the power supply 16. For at least a portion of the weld, the operator may desire to change the current. Accordingly, the operator may say "parameter adjust mode" or press a button on the welding helmet 42. The display 48 may switch from a working view to show a caricature of the power supply 16. Although the operator may use hand, head, and/or body gestures to select and modify parameters, the operator may be currently welding and may not want to disturb the arc 12. For example, for certain welds or certain types of welds (e.g., TIG vs. MIG), more sensitivity may be desired. As such, the operator may say "amps up by five" into a microphone in the welding helmet 42. The welding helmet 42 sends the command—either as raw audio, processed audio, or a digital representation of the command—to a control device, such as the power supply control circuitry 30. Once the control device receives the command as either a vocal command or gesture, the control device increases the current of the power supply 16.

Although the foregoing discussion relates generally to displaying power supply information, in some embodiments, other information may be displayed by the display 48 either as additional information or as alternative information. Specifically, the IMUs 46 or other sensors may determine parameters about the weld joint and/or process that may be indicative of a quality of the weld joint. For example, the IMUs 46 may be used to determine travel speed of the welding torch 26. This information may be displayed to the user via the display 48. Additionally or alternatively, welding instructions based on the determined parameters may be provided to the user via the display 48. For example, the display 48 may show an up arrow asking that the user increase speed, current, or voltage of the weld. Additionally or alternatively, the display 48 may instruct the user to modify orientation of the welding torch 26 in relation to the welding helmet 42 and/or workpiece 14.

Although the foregoing discussion generally relates to welding torches, in some embodiments, motion sensing may be used for any welding-type tool or accessory associated with a welding-type process. As used herein, welding-type refers to any process related to welding, such as welding, cutting, or gouging. Furthermore, a welding-type tool or accessory may be any tool or accessory using in such processes. For example, welding-type tools may include torches, electrode holders, machining tools, or other similar tools that may be used in the welding-type processes. Moreover, welding-type accessories may include wearable devices, such as a helmet, a jacket, a glove, a bracelet, or other devices that may be worn by an operator.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A welding system, comprising:
   a power supply configured to provide a welding power output;
   a welding helmet comprising:
      an electronic display configured to display a representation of the power supply and to display one or more indications of one or more parameters of the power supply, wherein the representation of the power supply includes at least one control element corresponding to at least one parameter of the one or more parameters; and
      a first inertial measurement unit configured to detect movement of the welding helmet by an operator; and
   a processing system communicatively coupled to the first inertial measurement unit and configured to adjust the at least one parameter of the one or more parameters during a weld process powered by the power supply based at least in part on data from the first inertial measurement unit,
   wherein the first inertial measurement unit is configured to detect at least one specific movement of the welding helmet corresponding to a user input by the operator to adjust a welding parameter of the power supply,
   wherein the processing system is configured to update the at least one control element on the representation of the power supply to reflect the adjusted welding parameter in response to the at least one specific movement of the welding helmet.

2. The welding system of claim 1, comprising a welding torch communicatively coupled to the power supply, wherein the welding torch comprises a second inertial measurement unit configured to detect movement of the welding torch, wherein the processing system is configured to adjust the at least one parameter of the one or more parameters based at least in part on the movement of the welding torch.

3. The welding system of claim 1, comprising a welding glove comprising a second inertial measurement unit configured to detect movement of the welding glove, wherein the processing system is configured to adjust the at least one parameter of the one or more parameters based at least in part on the movement of the welding glove.

4. The welding system of claim 1, wherein the at least one parameter comprises a current level of the power supply, a voltage level of the power supply, or a welding process type.

5. The welding system of claim 4, wherein the at least one parameter comprises a voltage for metal inert gas (MIG) welding, a current for shielded metal arc welding (SMAW), and a current for tungsten inert gas (TIG) welding.

6. The welding system of claim 1, wherein the processing system comprises power supply control circuitry.

7. The welding system of claim 1, wherein the first inertial measurement unit comprises at least one accelerometer or a gyroscope.

8. The welding system of claim 1, wherein the first inertial measurement unit is configured to detect one or more predefined gestures.

9. The welding system of claim 1, comprising a transceiver configured to transmit information indicative of the movement to the power supply.

10. The welding system of claim 1, wherein the electronic display comprises a transparent light emitting diode display or a transparent organic light emitting diode display.

11. The welding system of claim 1, wherein the welding helmet comprises a camera configured to capture images of a working view of a weld area, and the electronic display is configured to display the images.

12. A welding system, comprising:
a power supply;
a welding helmet comprising:
an electronic display configured to display a representation of the power supply and to display one or more indications of one or more parameters of the power supply, wherein the representation of the power supply includes at least one control element corresponding to at least one parameter of the one or more parameters; and
an audible command unit configured to receive audible commands by an operator; and
a processing system communicatively coupled to the audible command unit and configured to adjust at least one parameter of the one or more parameters during a weld process powered by the power supply and to update the one or more indications on the electronic display of one or more parameters based at least in part on data from the audible command unit,
wherein the adjustment of the at least one parameter is based at least in part on at least one specific audible command corresponding to a user input by the operator to adjust a welding parameter of the power supply, and
wherein the processing system is configured to update the at least one control element on the representation of the power supply to reflect the adjusted welding parameter in response to the at least one specific audible command.

13. The welding system of claim 12, comprising an inertial measurement unit configured to detect movements of the welding helmet, welding gloves, or a welding torch, wherein the processing system is configured to adjust the at least one parameter based at least in part on the detected movements of the welding helmet, the welding gloves, or the welding torch.

14. The welding system of claim 12, wherein the representation of the power supply comprises an image of the power supply, a simplified representation of the power supply, or a heads up display.

15. The welding system of claim 12, wherein the audible command unit comprises a microphone configured to receive the at least one specific audible command from the operator.

16. A welding system, comprising:
a power supply configured to provide a welding power output;
a welding helmet comprising:
an electronic display configured to display a representation of the power supply, one or more indications of one or more parameters of the power supply, and a cursor, wherein the representation of the power supply includes at least one control element corresponding to at least one parameter of the one or more parameters; and
an inertial measurement unit configured to detect movement of the welding helmet by an operator; and
a processing system communicatively coupled to the inertial measurement unit and configured to control the cursor during a weld process powered by the power supply based at least in part on data from the inertial measurement unit,
wherein the inertial measurement unit is configured to detect at least one specific movement of the welding helmet corresponding to a user input by the operator to adjust a welding parameter of the power supply, and
wherein the at least one specific movement of the welding helmet results in a manipulation of the cursor to adjust the welding parameter via the electronic display.

17. The welding system of claim 16, wherein the at least one control element is depicted on the electronic display as a dial or knob.

18. The welding system of claim 16, further comprising an audible command unit configured to receive audible commands by the operator.

19. The welding system of claim 18, wherein the processing system is configured to manipulate the cursor based at least in part on data from the audible command unit.

20. The welding system of claim 16, wherein the cursor is a box or an arrow.

* * * * *